(12) United States Patent
Moses et al.

(10) Patent No.: US 7,371,812 B2
(45) Date of Patent: May 13, 2008

(54) ANTIANGIOGENIC PEPTIDES

(75) Inventors: Marsha A. Moses, Brookline, MA (US); Cecilia A. Fernandez, Jamaica Plain, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 11/263,546

(22) Filed: Oct. 31, 2005

(65) Prior Publication Data
US 2006/0099684 A1    May 11, 2006

Related U.S. Application Data

(63) Continuation of application No. PCT/US04/13170, filed on Apr. 29, 2004.

(60) Provisional application No. 60/466,502, filed on Apr. 29, 2003.

(51) Int. Cl.
*C07K 14/00* (2006.01)
*A61K 38/00* (2006.01)

(52) U.S. Cl. .................. 530/325; 530/300; 514/13

(58) Field of Classification Search ............... 530/300
See application file for complete search history.

(56) References Cited

U.S. PATENT DOCUMENTS

2002/0086420 A1    7/2002    Moses et al.
2003/0027778 A1    2/2003    Fuqua et al.

FOREIGN PATENT DOCUMENTS

WO    WO 00/54796    *    9/2000

OTHER PUBLICATIONS

Stetler-Stevenson et al., *J. of Bio. Chem.*, 265:13933-13938 (Aug. 15, 1990).
Willenbrock et al., *Biochemistry*, 32:4330-4337 (1993).
Salmela et al., *British J. of Cancer*, 85(3): 383-392 (2001).

* cited by examiner

*Primary Examiner*—Karen Cochrane Carlson
*Assistant Examiner*—Suzanne M. Noakes
(74) *Attorney, Agent, or Firm*—Nixon Peabody LLP

(57) ABSTRACT

The present invention provides an antiangiogenic polypeptide having the amino acid sequence set forth in SEQ ID NO: 1, or a fragment thereof, which is effective to inhibit endothelial cell proliferation as determined by the capillary EC proliferation assay. Preferably, the fragment has at least 50% inhibition of bFGF-stimulated EC proliferation at 5 μg/ml-20 μg/ml, more preferably 75% inhibition, most preferably 95% inhibition.

19 Claims, 8 Drawing Sheets

```
         1                  11                 21                 31                 41
T1C   CTVFPCLSIPCKLQSGTHCLWTDQLLQGSEKGFQSRHLACLPREPGLCTW
T2C   CKITRCPMIPCYISSPDECLWMDWVTEKNINGHQAKFFACIKRSDGSCAW
T3C   CKIKSCYYLPCFVTSKNECLWTDMLSNFGYPGYQSKHYACIRQKGGYCSW
T4C   CQITTCYTVPCTISAPNECLWTDWLLERKLYGYQAQHYVCMKHVDGTCSW
CONSENSUS  C     C  PC       CLW D           Loop 6   G Q       G C W
                    Loop 5

51                 61
T1C   QSLRSQIA
T2C   YRGAAPPKQEFLDIEDP
T3C   YRGWAPPDKSISNATDP
T4C   YRGHLPLRKEFVDIVQP
CONSENSUS    Tail
```

*FIG. 1*

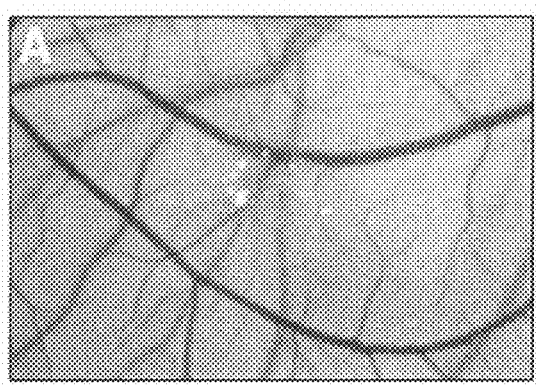
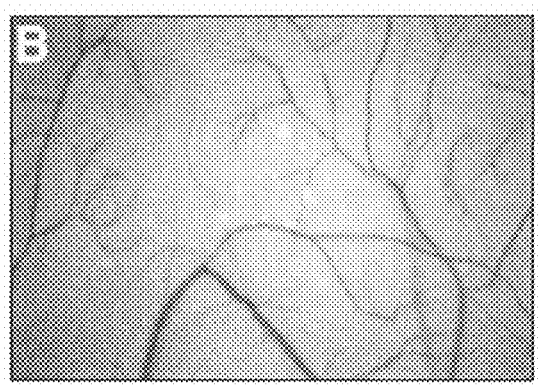
*FIG. 7A*  *FIG. 7B*
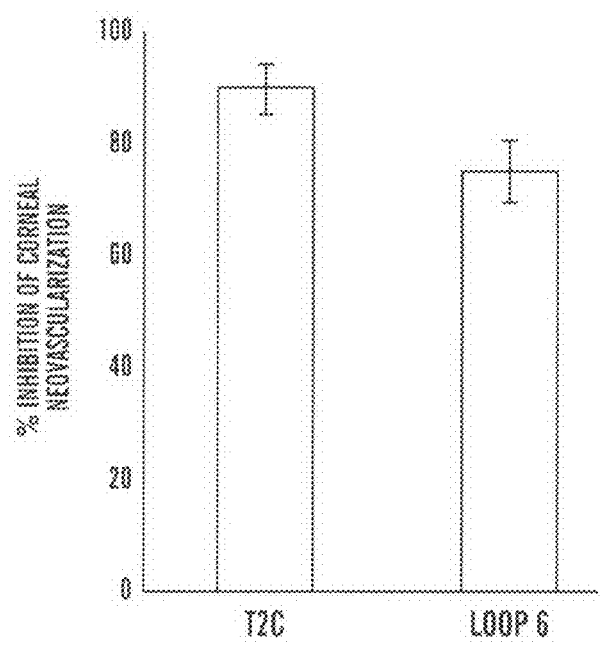
*FIG. 7C*

|  | LOOP 6 | bFGF | T2-TAIL |
|---|---|---|---|
| G1 | 45.60% | 26.8% | 27.8% |
| S | 37.70% | 29.2% | 32.9% |
| G2/M | 9.53% | 39.7% | 34.6% |

ANTIANGIOGENIC PEPTIDES

CROSS REFERENCED APPLICATIONS

This Application is a Continuation of International Application PCT/US2004/013170 filed on Apr. 29, 2004, which claims the benefit under 35 U.S.C. of U.S. Provisional Application No. 60/466,502 filed on Apr. 29, 2003.

FIELD OF THE INVENTION

The present invention provides a novel antiangiogenic polypeptide, analogs, fragments, or derivatives thereof, and method of use thereof for treatment of diseases or disorders involving abnormal angiogenesis and tissue remodeling-associated conditions.

BACKGROUND

Blood vessels are the means by which oxygen and nutrients are supplied to living tissues and waste products are removed from living tissue. Angiogenesis refers to the process by which new blood vessels are formed. See, for example, the review by Folkman and Shing, *J. Biol. Chem.* 267, 10931-10934 (1992). Thus, where appropriate, angiogenesis is a critical biological process. It is essential in reproduction, development and wound repair. However, inappropriate angiogenesis can have severe negative consequences. For example, it is only after many solid tumors are vascularized as a result of angiogenesis that the tumors have a sufficient supply of oxygen and nutrients that permit it to grow rapidly and metastasize. Because maintaining the rate of angiogenesis in its proper equilibrium is so critical to a range of functions, it must be carefully regulated in order to maintain health. The angiogenesis process is believed to begin with the degradation of the basement membrane by proteolytic enzymes, e.g., metalloproteinases (MMPs) and plasminogen activator (PA), secreted from endothelial cells (EC) activated by mitogens such as vascular endothelial growth factor (VEGF) and basic fibroblast growth factor (bFGF).

Proteolytic activity is also required for the migration of EC into the perivascular stroma. These events are followed by sprout extension and subsequent lumen formation (Ausprunk, D. H., et al., *Microvascular Res.* 14:53-65 (1977)). As is EC "escape" from the parent venule, capillary sprout elongation, lumen formation, and EC migration are all events which are dependent on a shift in the proteolytic balance in favor of enzymatic activity (Ausprunk, D. H., et al., *Microvascular Res.* 14:53-65 (1977), Kalebic, T., et al. *Science,* 221:281-283 (1983), and (Moses, M. A., et al., *Science* 248:1408-1410 (1990)). Vascular morphogenesis and invasion are also regulated by shifts in the finely tuned balance between proteases and their inhibitors (Liotta, L. A., et al., *Cell* 64:327-336, (1991); Moses, M. A., et al., *J. Cell Biochem.* 47:1-8 (1991); Herron, G. S., et al., *J. Biol. Chem.* 261:2814-2828 (1986), and Montesano, R., et. al., *Cell* 62:435-445, (1990)).

An accumulating body of evidence suggests that the remodeling of ECM that occurs during normal growth, wound repair and angiogenesis as well as during the development and progression of pathologic conditions including malignant diseases, is accomplished largely through the action of MMPs (Birkedal-Hansen, H. *Cell. Bio.* 7:728-735 (1985), Matrisian, L. *Trends Genet.* 6:121-125, (1990), and Woessner, J. F. *Acad. Sci.* 732:11-21 (1994), and Woessner, J. F. *Ann. N.Y. Acad. Sci.* 732:11-21, 1994).

The MMPs are members of a multigene family of metal-dependent enzymes. These proteases have been classified into four broad categories originally based on substrate specificity. These specific enzymes are the collagenases (MMP-1/EC3.4.24.7; MMP-8/EC3.4.24.34; MMP-13), the gelatinases A (MMP-2/EC3.4.24.24) and B(MMP-9/EC3.4.24.35), the stromelysins (MMP-3/EC3.4.24.17: MMP-10/EC3.4.24.22; MMP-1/EC3.4.24.7) including a metalloelastase (MMP-12), the membrane MMPs (MMP-14) (Birkedai-Hansen, H. *Current Opinions in Cell Biol.* 7:728-735, 1995. Matrisian, L. *Trends Genet.* 6:121-125, 1990. Woessner, J. F. *Ann. N.Y. Acad. Sci.* 732:11-21, 1994) and the family of membrane type MMPs (MT-MMP 1-6).

The regulation of MMP activity occurs at several levels including gene transcriptional control, proenzyme activation and inhibition of activated MMPs by endogenous inhibitors. Like many other enzyme families, the MMPs are a key component of a system of "balanced proteolysis" wherein a finely tuned equilibrium exists between the amount of active enzyme and its proteinase inhibitor(s) (Liotta, L. A., et al., *Cell* 64:327-336, (1991)). These native metalloproteinase inhibitors comprise a family of proteins generally referred to as the TIMPS (Tissue Inhibitor of MetalloProteinase) (Docherty, A. J. P., et al., *Nature* 318:66-69, (1985), Carmichael, D. F., et al. *Proc. Natl. Acad. Sci. USA* 83:2407-2411, (1986); Moses, M. A., et al., *J. Cell. Biochem.* 47:230-235, (1991); Murray, J. B., et al., *J. Biol. Chem.* 261:4154-4159 (1986); Stetler-Stevenson, W. G., et al., *J. Biol. Chem.* 29:17374-17378, (1989); Pavloff, N., et al., *J. Biol. Chem.* 267:17321-17326, (1992), and DeClerck, T. A., et al., *J. Biol. Chem.* 264:17445-17453 (1989)). They bind to activate MMPs with 1:1 molar stoichiometry.

The TIMPs consist of six disulfide-bonded loops. Deletion mutagenesis studies have demonstrated that two structurally distinct domains can be defined, the N-terminal domain consisting of loops 1-3 and the C-terminal domain consisting of loops 4-6 (Murphy, G. Houbrechts., et al. *Biochemistry* 30(33):8097-8101, (1991); Willenbrock, F., et al., *Biochem.* 32:4330-4337, (1993), and Nguyen, Q., et al., *Biochem.* 33:2089-2095, (1994)).

Much research attention has been focused on studies aimed at defining the domains of TIMPs that are important to their ability to inhibit MMP activity. Construction of truncated forms of these molecules has provided some insight. Residues 1-126 of TIMP-1 and 1-127 of TIMP-2 which contain three of the six disulfide bonds in the full-length molecules have been expressed in mammalian cells in the absence of the G-terminal region and are secreted in a soluble form (Murphy, G., et al. *Biochemistry* 30(33):8097-8101, (1991)). These truncated forms inhibit matrilysin and the catalytic domains of stromelysin and gelatinase A, demonstrating that there is a direct interaction between the N-terminal domain of the TIMPs and the catalytic domains of the MMPs (Murphy, G., et al. *Biochemistry* 30(33):8097-8101, (1991); Willenbrock, F., et al., *Biochem.* 32:4330-4337, (1993), and Nguyen, Q., et al., *Biochem.* 33:2089-2095, (1994). The structure of the N-terminal domain of either TIMP-1 or TIMP-2 is not affected by the C-terminal domain (Nguyen. Q., et al., *Biochemistry* 33:2089-2095, (1994)).

A significant number of mutational analyses also support the concept that the $NH_2$-terminal domain of TIMP-1 ($Cys^1$-$Glu^{126}$) is sufficient for inhibition of MMPs (Wilhelm, S. M., et al., *J. Biol. Chem.* 264:17213-17221, (1989), Murphy, G., et al., *Biochemistry* 30(33):8097-8101, (1991); Murphy, G., et al., *Bio. Chem. Biophys. Acta.* 839:214-218, (1985); Stricklin, G. P., *Collagen Relat. Res.* 6:219-228, (1986);

Tolley, S. P., et al., *Protein: Struc., Fuct., Genet.* 17:435-437, (1993), and Howard, E. W., et al., *J. Biol. Chem.* 266:13064-13069, (1991)). Furthermore, single-residue mutations in the region bounded by Cys3 and Cys13 caused an increase of 8-fold in Ki when compared with wild type TIMP-1 (O'Shea, M., et al., *Biochemistry* 31(42):10146-10151, (1992)). A series of experiments including competition studies with synthetic peptides and localization of epitopes of blocking antibodies revealed that the region marking the transition between the NH2-terminal and COOH-terminal domains of the TIMP-1 molecule may be particularly important for its ability to inhibit collagenase (Bodden, M. K., et al., *J. Biol. Chem.* 269:18943-18952, (1994)).

It is now widely accepted that the N-terminal domain of the TIMPs represent a stable, minimized form of the inhibitor that includes the major site or sites necessary for MMP inhibition (Williamson, R. A., et al., *Biochem.* 33:11745-11759, (1994)). Site-directed mutagenesis studies on TIMP-1 have demonstrated that no single residue is likely to be responsible for MMP inhibition (O'Shea, M., et al., *Biochem.* 31(42): 10146-10151, (1992)).

The C-terminal domain of TIMPs also makes some binding contribution to the TIMP-MMP complex, in particular, the C-terminal domain of TIMP-2 which may be responsible for the specific interaction of this molecule with progelatinase A (Willenbrock, F., et al., *Biochemistry* 32:4330-4337, (1993)). Mutational studies also support the idea that the COOH-terminal domain of TIMP-2 which does not appear to be required for MMP inhibition (O'Shea, M., et al., *Biochemistry* 31(42):10146-10151 (1992)) interacts with the pexin-like domain of gelatinase A (Hayakawa, T., et al., *FEBS Lett.* 298:29-32, (1992)). This interaction has been shown to prevent autodegradation of the enzyme (Goldberg, G. I., et al., *J. Biol. Chem.* 267:4583-4591 (1992), Bodden, M. K., et al., *Biol. Chem.* 269:18943-18952, (1994), and Howard, E. W., et al., *J. Biol. Chem.* 266:13084-13089, (1991)).

TIMPs have been shown to inhibit the migration of endothelial cells in vitro and, depending on the model used, angiogenesis in vivo. Mignatti, et al. (*J. Cell Bio.* 108:671-682, (1989)) first demonstrated that TIMP-1 could inhibit migration of microvascular cells in vitro using the amnion invasion assay. Montesano and coworkers later showed that a collagenase inhibitor (1,10-phenanthroline) could inhibit capillary tube formation in vitro (Montesano, R., et. al. *Cell* 42:489-477, (1985)). Since it was first demonstrated that a TIMP purified from a vascular cartilage was a potent inhibitor of angiogenesis in vivo and EC proliferation and migration in vitro (Moses, M. A., et al., *Science* 248:1408-1410, (1990); Moses, M. A., et al., *J. Cell Biol.* 119:475-482, (1992) and Murphy, A. N. et al., *J. Cell. Phys.* 157:351-358 (1993)) showed that TIMP-2, but not TIMP-1, inhibited FGF-stimulated endothelial cell proliferation. TIMP-1 has been shown to stimulate the growth of EC proliferation in other studies as well (Hayakawa, T., et al *FEBS Letts.* 298:29-32, (1992)). TIMPs have been shown to inhibit neovascularization in various in vivo models (Takigawa, M., et al., *Biochem. Biophys. Res. Commun.* 171:1264-1271 and Johnson, M. D. et al., *J. Cell. Physiol.* 160:194-202, (1989)).

Much research attention has focused on studies aimed at defining the domain of TIMPs that are important to their ability to inhibit MMP activity. It is now widely accepted that the N-terminal domain of the TIMPs represents a stable, minimized form of the inhibitor that includes the major site or sites necessary for MMP inhibition (Williamson, R. A. et al. *Biochemistry* 33:11745-11759 (1994)). The C-terminal domain of TIMPs also makes some binding contribution to the TIMP-MMP complex, in particular, the C-terminal domain of TIMP-2 which may be responsible for the specific interaction of this molecule with progelatinase A (Willenbrock, F. et al., *Biochemistry* 32:4330-4337 (1993)).

It has been suggested that the regions of amino acid sequences between TIMP-1 and TIMP-2 that are highly conserved such as the N-terminus, may be responsible for the known shared functions of these proteins, for example, inhibition of activated MMPs and their shared ability to inhibit FGF-stimulated capillary EC migration (Moses, M. A. et al., *Science* 248:1408-1410 (1990); Moses, M. A. et al., *J. Cell Biol.* 119:475-482 (1992); Mignatti, P. et al., *J. Cell Bio.* 108:671-682 (1989) and Murphy, A. N. et al., *J. Cell. Phys.* 157:351-358 (1993)). Areas of low homology, for example, the C-terminus, may be responsible for those functions which are unique for the individual TIMPs (Stetler-Stevenson et al., *J. Biol. Chem.* 265(23)13933-13936 (1990)). These include the binding of TIMP-2 to the latent form of gelatinase A and the failure of TIMP-2 antibodies to detect TIMP-1 (Stetler-Stevenson, W. G. et al., *J. Biol. Chem.* 265(23):13933-13936 (1990).

The rate of angiogenesis involves a change in the local equilibrium between positive and negative regulators of the growth of microvessels. The therapeutic implications of angiogenic growth factors were first described by Folkman and colleagues over two decades ago (Folkman, *N. Engl. J. Med.,* 285:1182-1186 (1971)). Abnormal angiogenesis occurs when the body loses at least some control of angiogenesis, resulting in either excessive or insufficient blood vessel growth. For instance, conditions such as ulcers, strokes, and heart attacks may result from the absence of angiogenesis normally required for natural healing. In contrast, excessive blood vessel proliferation can result in tumor growth, tumor spread, blindness, psoriasis and rheumatoid arthritis.

Thus, there are instances where a greater degree of angiogenesis is desirable-increasing blood circulation, wound healing, and ulcer healing. For example, recent investigations have established the feasibility of using recombinant angiogenic growth factors, such as fibroblast growth factor (FGF) family (Yanagisawa-Miwa, et al., *Science,* 257:1401-1403 (1992) and Baffour, et al., *J Vasc Surg,* 16:181-91 (1992)), endothelial cell growth factor (ECGF) (Pu, et al., *J Surg Res,* 54:575-83 (1993)), and more recently, vascular endothelial growth factor (VEGF) to expedite and/or augment collateral artery development in animal models of myocardial and hindlimb ischemia (Takeshita, et al., *Circulation,* 90:228-234 (1994) and Takeshita, et al., *J Clin Invest,* 93:662-70 (1994)).

Conversely, there are instances, where inhibition of angiogenesis is desirable. For example, many diseases are driven by persistent unregulated angiogenesis, also sometimes referred to as "neovascularization." In arthritis, new capillary blood vessels invade the joint and destroy cartilage. In diabetes, new capillaries invade the vitreous, bleed, and cause blindness. Ocular neovascularization is the most common cause of blindness. Tumor growth and metastasis are angiogenesis-dependent. A tumor must continuously stimulate the growth of new capillary blood vessels for the tumor itself to grow.

The current treatment of these diseases is inadequate. Agents which prevent continued angiogenesis, e.g., drugs (TNP-470), monoclonal antibodies, antisense nucleic acids and proteins (angiostatin and endostatin) are currently being tested. See, Battegay, *J. Mol. Med.,* 73, 333-346 (1995); Hanahan et al., *Cell,* 86, 353-364 (1996); Folkman, *N. Engl. J. Med.,* 333, 1757-1763 (1995). Although preliminary results with the antiangiogenic proteins are promising, they are relatively large in size and they are difficult to use and produce. Moreover, proteins are subject to enzymatic degradation. Thus, new agents that inhibit angiogenesis are needed. New antiangeogenic peptides that show improvement in size, ease of production, stability and/or potency would be desirable.

SUMMARY OF THE INVENTION

We have surprisingly discovered that a 24 amino acid peptide fragment corresponding to Loop 6 of the carboxy terminus of TIMP-2 protein, does not inhibit MMP activity but has endothelial cell inhibitory activity, i.e., the ability to inhibit endothelial cell proliferation. Thus, this fragment is useful as an antiangiogenic agent.

The present invention provides an antiangiogenic polypeptide having the amino acid sequence ECLWMD-WVTEKNINGHQAKFFACI (SEQ ID NO: 1) or a fragment thereof, which is effective to inhibit endothelial cell proliferation as determined by the capillary EC proliferation assay. Preferably, the fragment has at least 50% inhibition of bFGF-stimulated EC proliferation at between 5 μg/ml-20 μg/ml, more preferably 75% inhibition, most preferably 95% inhibition.

One embodiment of the invention provides for molecules consisting of, or comprising, a fragment of at least 4 (contiguous) amino acids of the antiangiogenic polypeptide which is capable of inhibiting endothelial cell proliferation as discussed above. In other embodiments, this molecule consists of at least 8, 10 or 20 amino acids of the antiangiogenic polypeptide.

The present invention further includes an antiangiogenic polypeptide having at least 80% identity compared to SEQ ID No: 1, or a fragment thereof, as defined above. In one embodiment, this identity is greater than 85%. In another embodiment, this identity is greater than 90%. In a more preferred embodiment, the amino acid sequence of the peptide has at least 95% identity with SEQ ID NO: 1, or a fragment thereof, as defined above. In another embodiment, the invention encompasses a peptide encoded by a nucleic acid hybridizable to the complement of a nucleic acid encoding a SEQ ID NO: 1, under low stringency, moderate stringency or high stringency conditions.

Analogs and derivatives of the antiangiogenic polypeptide of the invention are further included in the present invention.

The present invention also provides pharmaceutical compositions comprising antiangiogenic polypeptide, analogs or derivative thereof, or nucleic acid encoding such polypeptides, in a therapeutically effective amount that is capable of inhibiting endothelial cell proliferation, and methods of use thereof.

The invention further provides methods for treatment or prevention of angiogenic disorders by administration of a pharmaceutical composition comprising an antiangiogenic polypeptide of the invention, or nucleic acid encoding such a polypeptide, and a pharmaceutically acceptable carrier.

In one embodiment, a pharmaceutical composition of the invention is administered to treat a cancerous condition, or to prevent progression from the pre-neoplastic or pre-malignant state into a neoplastic or a malignant state.

In another embodiment, a pharmaceutical composition of the invention is administered to treat restenosis.

In other specific embodiments, a pharmaceutical composition of the invention is administered to treat ocular disorders associated with neovascularization, such as retinopathy, diabetic retinopathy or macular degeneration.

The invention also provides methods for treatment of a class of disorders characterized as tissue remodeling-associated conditions, which include arthritic conditions, obstructive disorders, degenerative disorders, and problematic wound-healing and ulcerative disorders.

The methods of the present invention can be used either alone, or in conjunction with other treatment methods known to those of skill in the art. Such methods may include, but are not limited to, chemotherapy, radiation therapy, or other known angiogenesis inhibitors.

In yet another embodiment of the present invention, said administering comprises intravenous, transdermal, intrasynovial, intramuscular, or oral administration. Alternatively, administration of the antiangiogenic polypeptide of the invention may comprise administering a gene therapy vector that constitutively expresses the polypeptide of the invention, or fragment thereof.

The methods of the present invention also allow for the administration of the antiangiogenic polypeptide of the invention analogs, or derivatives thereof either prophylactically or therapeutically.

The risk of developing a disease or disorder for treatment by methods of the present invention can be determined genetically. Alternatively, the risk can be determined by measuring levels of a biomarker in the biological fluids (i.e. blood, urine) of a patient. For example, cancer marker proteins such as, calcitonin, PSA, thymosin β-15, thymosin β-16, and matrix metalloproteinase (MMP).

Other aspects of the invention are disclosed infra.

BRIEF DESCRIPTION OF THE FIGURES

FIG. 1 shows the sequence alignment of the C-terminal domains of human TIMPs 1-4. Residue 1 in each case is the first cysteine of the C-terminal domain, which corresponds to Cys127 of TIMP-1, Cys128 of TIMP-2, Cys122 of TIMP-3 and Cys129 of TIMP-4. Conserved residues are highlighted and indicated below the sequence alignment. The locations of the synthetic peptides of TIMP-2 used in this study are underlined. Sequence T1C is SEQ ID NO: 5, T2C is SEQ ID NO: 6, T3C is SEQ ID NO: 7, and T4C is SEQ ID NO: 8.

FIG. 2A is a schematic of TIMP-2 domains generated by PCR amplification. FIG. 2B shows a representative chromatogram of purification of T2C by reverse phase HPLC. FIG. 2C shows a silver stained SDS-PAGE gel of the His-affinity purified HPLC starting material of T2C (Lane 1) and the purified T2C (Lane 2) after reverse phase HPLC along with the EA-T2N construct that is deficient in MMP inhibitory activity. FIG. 2D shows a silver-stained SDS-PAGE gel of each of the expressed TIMP-2 and TIMP-2 domains.

FIG. 3A shows the effect of TIMP-2 domains on MMP activity using a radiometric collagen film assay. FIG. 3B shows the effect of TIMP-2 domains on capillary EC proliferation using a standard EC proliferation assay.

FIG. 4A, T2C; FIG. 4B, T2N, FIG. 4C, EA-T2N, FIG. 4D, intact TIMP-2.

FIG. 6A illustrates the synthetic peptides tested in relation to intact TIMP-2. FIG. 6B shows the effect of loop 6, T2-tail, and loop 5 on EC proliferation using an EC proliferation assay. FIG. 6C shows an FGF competition assay indicating that Loop 6 does not compete with FGF to inhibit capillary EC proliferation.

FIGS. 7A to 7C show that loop 6 inhibits embryonic and mitogen-stimulated angiogenesis in vivo. FIG. 7A shows the effect of loop 6 in a chick chorioallantoic membrane assay on neovascularization. FIG. 7B shows the effects of loop 6 on corneal neovascularization in the mouse corneal pocket assay. FIG. 7C shows the average percent inhibition of corneal neovascularization with T2C or loop 6 in a mouse corneal pocket assay.

FIG. 8A shows the percentages of cells found at the various stages of cell cycle in samples treated with FGF, or and IC50 dose of loop 6 or T2-tail peptide. FIG. 8B shows a Western analysis of cell cycle associated proteins in the lysates of bFGF-stimulated controls (Lane 1) versus bFGF-stimulated capillary EC treated with Loop 6 (Lane 2).

DETAILED DESCRIPTION OF THE INVENTION

Figure 2B:
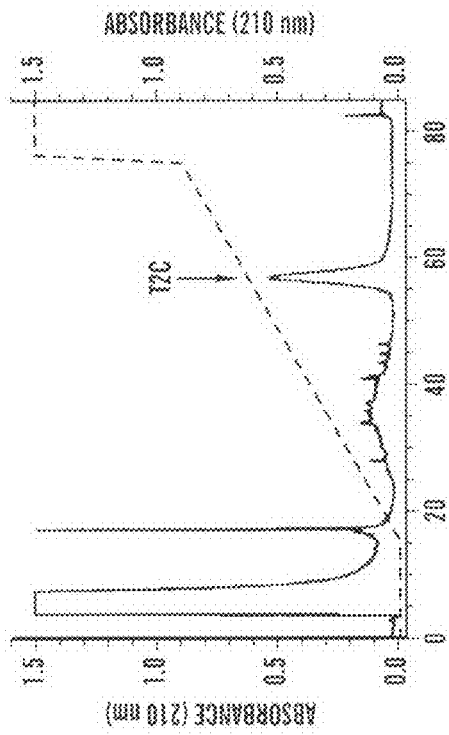
FIGS. 2A to 2D show expression and purification of TIMP-2 and TIMP-2 domains.

The present invention provides an antiangiogenic polypeptide having the amino acid sequence set forth in SEQ ID NO: 1, or a fragment thereof, which is effective to inhibit endothelial cell proliferation as determined by the capillary EC proliferation assay. Preferably, the fragment has at least 50% inhibition of bFGF-stimulated EC proliferation at 5 µg/ml-20 µg/ml, more preferably 75% inhibition, most preferably 95% inhibition.

It should be understood that a subject polypeptide need not be identical to the amino acid sequence set forth in SEQ ID. NO 1, or to the fragment thereof, so long as it has 50% identity and has endothelial cell proliferation inhibiting activity. In one embodiment, the antiangiogenic polypeptide of the invention has at least 80% identity to the amino acid sequence set forth in SEQ ID. NO 1, or fragment thereof. In another embodiment, the antiangiogenic polypeptide of the invention has at least 85% identity to the amino acid sequence set forth in SEQ ID. NO 1, or fragment thereof. In one preferred embodiment, the antiangiogenic polypeptide of the invention has at least 90% identity to the amino acid sequence set forth in SEQ ID. NO 1, or fragment thereof. Preferably, the antiangiogenic polypeptide of the invention contains 2 or more conserved amino acids, for example the conserved amino acids depicted in FIG. 1.

A subject polypeptide includes any analog, fragment or chemical derivative of a polypeptide whose amino acid residue sequence is shown herein so long as the polypeptide inhibits endothelial cell proliferation as described herein. Therefore, a present polypeptide can be subject to various changes, substitutions, insertions, and deletions where such changes provide for certain advantages in its use. In this regard, the antiangiogenic polypeptide of this invention corresponds to, rather than is identical to, the sequence of a recited peptide where one or more changes are made and it retains the ability to function as an angiogenesis inhibitor in one or more of the assays as defined herein.

Thus, a polypeptide can be in any of a variety of forms of peptide derivatives, which include amides, conjugates with proteins, cyclic peptides, polymerized peptides, analogs, fragments, chemically modified peptides, and the like derivatives.

The term "analog" includes any polypeptide having an amino acid residue sequence substantially identical to a sequence specifically shown herein or fragment thereof, in which one or more residues have been conservatively substituted with a functionally similar residue and which displays endothelial cell proliferation inhibitory activity as described herein. Examples of conservative substitutions include the substitution of one non-polar (hydrophobic) residue for another, such as the non-polar residues isoleucine, valine, leucine or methionine; the substitution of one polar (hydrophilic) residue for another, such as between arginine and lysine, between glutamine and asparagine, between glycine and serine; the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such polypeptide displays the requisite inhibition activity.

A "chemical derivative" refers to a subject polypeptide having one or more residues chemically derivatized by reaction of a functional side group. In addition to side group derivitations, a chemical derivative can have one or more backbone modifications including alpha-amino substitutions such as N-methyl, N-ethyl, N-propyl and the like, and alpha-carbonyl substitutions such as thioester, thioamide, guanidino and the like. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For examples: 4-hydroxyproline may be substituted for praline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained.

The term "fragment" refers to any subject polypeptide having an amino acid residue sequence shorter than that of a polypeptide whose amino acid residue sequence is shown herein.

When an antiangiogenic polypeptide of the present invention has a sequence that is not identical to the sequence of SEQ ID NO: 1, or fragment thereof, it is typically because one or more conservative or non-conservative substitutions have been made, usually no more than about 30 percent, and preferably no more than 10 percent of the amino acid residues are substituted. Additional residues may also be added at either terminus of a polypeptide for the purpose of providing a "linker" by which the polypeptides of this invention can be conveniently affixed to a label or solid matrix, or carrier.

Labels, solid matrices and carriers that can be used with the polypeptides of this invention are described herein.

Amino acid residue linkers are usually at least one residue and can be 40 or more residues, more often 1 to 10 residues. Typical amino acid residues used for linking are tyrosine, cysteine, lysine, glutamic and aspartic acid, or the like. In addition, a subject polypeptide can differ, unless otherwise specified, from the natural sequence of calcitonin by the sequence being modified by terminal-$NH_2$ acylation, e.g., acetylation, or thioglycolic acid amidation, by terminal-carboxylamidation, e.g., with ammonia, methylamine, and the like terminal modifications. Terminal modifications are useful, as is well known, to reduce susceptibility by proteinase digestion, and therefore serve to prolong half life of the polypeptides in solutions, particularly biological fluids where proteases may be present.

Mimetics also can be used in accordance with the present invention to inhibit angiogenesis. The design of mimetics is known to those skilled in the art, and is generally understood to be peptides or other relatively small molecules that have an activity the same or similar to that of a larger molecule, often a protein, on which they are modeled.

The antiangiogenic polypeptide and analogs of the invention can be derived from tissue or produced by various methods known in the art. The manipulations, which result in their production, can occur at the gene or protein level. For example, a cloned gene sequence coding for an antiangiogenic polypeptide can be modified by any of numerous strategies known in the art. See, Sambrook et al., 2001, Molecular Cloning, A Laboratory Manual, third edition., Cold Spring Harbor Laboratory, Cold Spring Harbor, N.Y. The sequence can be cleaved at appropriate sites with restriction endonuclease(s), followed by further enzymatic modification if desired, isolated, and ligated in vitro. In the production of the gene encoding a derivative or analog, care should be taken to ensure that the modified gene remains within the same translational reading frame as the native subunit gene, uninterrupted by translational stop signals, in the gene region where the desired activity is encoded.

The term "isolated" means that the polypeptide is removed from its original environment. For example, a naturally-occurring polynucleotide or polypeptide present in a living animal is not isolated, but the same polynucleotide or DNA or polypeptides, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The antiangiogenic polypeptide can be produced using peptide synthesis techniques or produced by recombinant methods, including, for example, the yeast expression system *Pichia pastoris*.

Peptide synthesis techniques are well known in the art. Synthetic chemistry techniques, such as a solid-phase Merrifield-type synthesis, are preferred for reasons of purity, antigenic specificity, freedom from undesired side products, ease of production and the like. An excellent summary of the many techniques available can be found in Steward et al., "Solid Phase Peptide Synthesis", W. H. Freeman Co., San Francisco, 1969; Bodanszky, et al., "Peptide Synthesis", John Wiley & Sons, Second Edition, 1976; J. Meienhofer, "Hormonal Proteins and Peptides", Vol. 2, p. 46, Academic Press (New York), 1983; Merrifield, Adv. Enzymol., 32:221-96, 1969; Fields et al., Int. J. Peptide Protein Res., 35:161-214, 1990; and U.S. Pat. No. 4,244,946 for solid phase peptide synthesis, and Schroder et al., "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final linear polypeptide.

The resultant linear polypeptides prepared for example as described above may be reacted to form their corresponding cyclic peptides. An exemplary method for preparing a cyclic peptide is described by Zimmer et al., Peptides (1992), pp. 393-394, ESCOM Science Publishers, B.V., 1993. Typically, tertbutoxycarbonyl protected peptide methyl ester is dissolved in methanol and sodium hydroxide solution are added and the admixture is reacted at 20° C. to hydrolytically remove the methyl ester protecting group. After evaporating the solvent, the tertbutoxycarbonyl protected peptide is extracted with ethyl acetate from acidified aqueous solvent. The tertbutoxycarbonyl protecting group is then removed under mildly acidic conditions in dioxane cosolvent. The unprotected linear peptide with free amino and carboxy termini so obtained is converted to its corresponding cyclic peptide by reacting a dilute solution of the linear peptide, in a mixture of dichloromethane and dimethylformamide, with dicyclohexylcarbodiimide in the presence of 1-hydroxybenzotriazole and N-methylmorpholine. The resultant cyclic peptide is then purified by chromatography. Alternative methods for cyclic peptide synthesis are described by Gurrath et al., Eur. J. Biochem., 210:911-921 (1992).

In addition, the antiangiogenic polypeptide of the invention, fragment, analog, or derivative thereof can be provided in the form of a fusion protein. Fusion proteins are proteins produced by recombinant DNA methods as described herein in which the subject polypeptide is expressed as a fusion with a second carrier protein such as a glutathione sulfhydryl transferase (GST), or other well known carrier.

Where it is desired to express a polypeptide of the invention any suitable system can be used. The general nature of suitable vectors, expression vectors and constructions therefore will be apparent to those skilled in the art.

Suitable expression vectors may be based on phages or plasmids, both of which are generally host-specific, although these can often be engineered for other hosts. Other suitable vectors include cosmids and retroviruses, and any other vehicles, which may or may not be specific for a given system. Control sequences, such as recognition, promoter, operator, inducer, terminator and other sequences essential and/or useful in the regulation of expression, will be readily apparent to those skilled in the art.

Correct preparation of nucleotide sequences may be confirmed, for example, by the method of Sanger et al. (*Proc. Natl. Acad. Sci.* USA 74:5463-7 (1977)).

A DNA fragment encoding an antiangiogenic polypeptide may readily be inserted into a suitable vector. Ideally, the receiving vector has suitable restriction sites for ease of insertion, but blunt-end ligation, for example, may also be used, although this may lead to uncertainty over reading frame and direction of insertion. In such an instance, it is a matter of course to test transformants for expression, 1 in 6 of which should have the correct reading frame. Suitable vectors may be selected as a matter of course by those skilled in the art according to the expression system desired.

By transforming a suitable organism or, preferably, eukaryotic cell line, such as HeLa, with the plasmid obtained, selecting the transformant with ampicillin or by other suitable means if required, and adding tryptophan or other suitable promoter-inducer (such as indoleacrylic acid) if necessary, the desired polypeptide or protein may be expressed. The extent of expression may be analyzed by SDS polyacrylamide gel electrophoresis-SDS-PAGE (Lemelli, *Nature* 227:680-685 (1970)).

Suitable methods for growing and transforming cultures etc. are usefully illustrated in, for example, *Molecular Cloning, A Laboratory Manual* (3rd Ed., Sambrook, Fritsch and Maniatis, Cold Spring Harbor), *Current Protocols in Molecular Biology* (Eds. Aufubel, Brent, Kingston, More, Feidman, Smith and Stuhl, Greene Publ. Assoc., Wiley-Interscience, NY, N.Y. 1992).

The polypeptides and proteins may be isolated from the fermentation or cell culture and purified using any of a variety of conventional methods including: liquid chromatography such as normal or reversed phase, using HPLC, FPLC and the like; affinity chromatography (such as with inorganic ligands or antibodies); size exclusion chromatography; immobilized metal chelate chromatography; gel electrophoresis; and the like. One of skill in the art may select the most appropriate isolation and purification techniques without departing from the scope of this invention.

The functional activity and/or therapeutically effective dose of an antiangiogenic polypeptide or nucleic acid encoding therefor can be assayed in vitro by various methods. For example, where one is assaying for the ability of the angiogenic inhibitory polypeptide, fragments, and analogs, to inhibit or interfere with the proliferation of capillary endothelial cells (EC) in vitro, various bioassays known in the art can be used, including, but not limited to, radioactive incorporation into nucleic acids, calorimetric assays and cell counting.

Inhibition of endothelial cell proliferation may be measured by colorimetric determination of cellular acid phosphatase activity or electronic cell counting. These methods provide a quick and sensitive screen for determining the number of endothelial cells in culture after treatment with the connective tissue growth factor protein, derivative, or analog of the invention, and an angiogenesis stimulating factor such as aFGF, bFGF, or VEGF. The colorimetric determination of cellular acid phosphatase activity is described by Connolly et al., 1986, *J. Anal. Biochem.* 152: 136-140. According to this method, capillary endothelial cells are treated with angiogenesis stimulating factors, such as aFGF, bFGF, or VEGF, and a range of potential inhibitor concentrations. These samples are incubated to allow for growth, and then harvested, washed, lysed in a buffer containing a phosphatase substrate, and then incubated a second time. A basic solution is added to stop the reaction and color development is determined at 405λ. According to Connolly et al., a linear relationship is obtained between acid phosphatase activity and endothelial cell number up to 10,000 cells/sample. Standard curves for acid phosphatase activity are also generated from known cell numbers in order to confirm that the enzyme levels reflect the actual EC numbers. Percent inhibition is determined by comparing the cell number of samples exposed to stimulus with those exposed to both stimulus and inhibitor.

The incorporation of radioactive thymidine by capillary endothelial cells represents another means by which to assay for the inhibition of endothelial cell proliferation by a potential angiogenesis inhibitor. According to this method, a predetermined number of capillary endothelial cells are grown in the presence of $^3$H-Thymidine stock, an angiogenesis stimulator such as for example, bFGF, and a range of concentrations of the angiogenesis inhibitor to be tested. Following incubation, the cells are harvested and the extent of thymidine incorporation is determined.

The ability of varying concentrations of the antiangiogenic polypeptide to interfere with the process of capillary endothelial cell migration in response to an angiogenic stimulus can be assayed using the modified Boyden chamber technique.

Another means by which to assay the functional activity of the antiangiogenic polypeptide involves examining the ability of the compounds to inhibit the directed migration of capillary endothelial cells which ultimately results in capillary tube formation. This ability may be assessed for example, using an assay in which capillary endothelial cells plated on collagen gels are challenged with the inhibitor, and determining whether capillary-like tube structures are formed by the cultured endothelial cells.

Assays for the ability to inhibit angiogenesis in vivo include the chick chorioallantoic membrane assay and mouse, rat or rabbit corneal pocket assays. See, Polverini et al., 1991, *Methods Enzymol.* 198: 440-450. In corneal pocket assays, an angiogenic mitogen, e.g. FGF or VEGF, or a tumor of choice is implanted into the cornea of the test animal in the form of a corneal pocket. The potential angiogenesis inhibitor is applied to the corneal pocket and the corneal pocket is routinely examined for neovascularization.

The ability of the antiangiogenic polypeptides to influence angiogenesis can also be determined using a number of known in vivo and in vitro assays. Such assays are disclosed in Jain et al., *Nature Medicine* 3, 1203-1208 (1997), the disclosure of which is herein incorporated by reference.

The therapeutically effective dosage for inhibition of angiogenesis in vivo, defined as inhibition of capillary endothelial cell proliferation, migration, and/or blood vessel growth, may be extrapolated from in vitro inhibition assays using the compositions of the invention above or in combination with other angiogenesis inhibiting factors. The effective dosage is also dependent on the method and means of delivery. For example, in some applications, as in the treatment of psoriasis or diabetic retinopathy, the inhibitor is delivered in a topical-ophthalmic carrier. In other applications, as in the treatment of solid tumors, the inhibitor is delivered by means of a biodegradable, polymeric implant. The protein can also be modified, for example, by polyethyleneglycol treatment.

In general, it is desirable to provide the recipient with a dosage of antiangiogenic peptide of the invention of at least about 0.1 µg/kg, preferably at least about 25 µg/kg, more preferably at least about 50 µg/kg or higher. A range of from about 1 µg/kg to about 100 µg/kg is preferred although a lower or higher dose may be administered. The dose provides an effective antiangiogenic serum or tissue level of the antigangiogenic peptide of the invention. The dose is administered at least once and may be provided as a bolus, a continuous administration, pulsed administration, or sustained release. Multiple administration over a period of weeks or months may be preferable. It may also be preferable to administer polypeptide at least once/week and even more frequent administrations (e.g. daily). Subsequent doses may be administered as indicated.

The antiangiogenic polypeptide of the invention, fragments, analogs, or derivatives thereof can be combined with a therapeutically effective amount of another molecule which inhibits angiogenesis, or can be combined with other therapies such as conventional chemotherapy or radiation therapy often directed against solid tumors and metastases. The administration of angiogenesis-inhibiting amounts of the antiangiogenic polypeptide of the invention, fragments, analogs, or derivatives thereof may be conducted before, during or after chemotherapy or radiation therapy. Known angiogenesis inhibitors that may used in methods of the invention include, but are not limited to, both direct and indirect angiogenesis inhibitors such as Angiostatin, Bevacizumab (Avastin), Arresten, Canstatin, Combretastatin, Endostatin, NM-3, Thrombospondin, Tumstatin, 2-methoxyestradiol, and Vitaxin, ZD1839 (Iressa), ZD6474, OSI774 (Tarceva), CI1033, PKI1666, IMC225 (Erbitux), PTK787, SU6668, SU11248, Herceptin, Marimastat, COL-3, Neovastat, 2-ME, SU6668, anti-VEGF antibody, Medi-522 (Vitaxin II), tumstatin, arrestin, recombinant EPO, troponin I, EMD121974, and IFN-α. CELEBREX® (Celecoxib), and THALOMID® (Thalidomide), have also been recognized as angiogenesis inhibitors (Kerbel et al., Nature Reviews, Vol. 2, October 2002, pp. 727). For combination therapy, the dose of the antiangiogenic polypeptide of the invention, fragment, analog, or derivative thereof may be administered prior to, concurrently, or after administration of a second antiangiogenic agent or chemotherapeutic agent. Furthermore, the compounds of the present invention may be administered alone or in combination with another antiangiogenic compound prior to, concurrently, or after the surgical removal of a solid tumor mass.

In the method of treatment, the administration of the antiangiogenic polypeptide of the invention, fragment, analog, or derivative thereof may be for either "prophylactic" or "therapeutic" purpose. When provided prophylactically, the polypeptide of the invention is provided in advance of any symptom. The prophylactic administration of the polypeptide serves to prevent or inhibit an angiogenesis disease or disorder, i.e. cancer. Prophylactic administration of the polypeptide of the invention may be given to a patient with, for example, a family history of cancer. Alternatively, administration of the antiangiogenic polypeptide of the invention may be given to a patient with rising cancer marker protein levels. Such markers include, for example, rising PSA, thymosin β-15, thymosin β-16, calcitonin, and matrix metalloproteinase (MMP).

When provided therapeutically, the polypeptide of the invention is provided at (or after) the onset of a symptom or indication of angiogenesis. Thus, the antiangiogenic polypeptide of the invention, fragment, analog, or derivative thereof may be provided either prior to the anticipated angiogenesis at a site or after the angiogenesis has begun at a site.

Insofar as the present methods apply to inhibition of tumor neovascularization, the methods can also apply to inhibition of tumor tissue growth, to inhibition of tumor metastases formation, and to regression of established tumors.

Restenosis is a process of smooth muscle cell (SMC) migration and proliferation at the site of percutaneous transluminal coronary angioplasty which hampers the success of angioplasty. The migration and proliferation of SMC's during restenosis can be considered a process of angiogenesis which is inhibited by the present methods. Therefore, the invention also contemplates inhibition of restenosis by inhibiting angiogenesis according to the present methods in a patient following angioplasty procedures. For inhibition of restenosis, an angiogenesis-inhibiting amount of the antiangiogenic polypeptide of the invention, fragment, analog, or derivative thereof is typically administered after the angioplasty. The administration of the compounds of the invention may occur from about 2 to about 28 days post-angioplasty and more typically for about the first 14 days following the procedure.

Diseases, disorders or conditions associated with abnormal angiogenesis or neovascularization that can be treated with a therapeutic compound of the invention include, but are not limited to retinal neovascularization, tumor growth, hemangioma, solid tumors, leukemia, metastasis, psoriasis, neovascular glaucoma, diabetic retinopathy, arthritis, endometriosis, and retinopathy of prematurity (ROP).

The term "effective amount" refers to an amount of the antiangiogenic polypeptide of the invention sufficient to exhibit a detectable therapeutic effect. The therapeutic effect may include, for example, without limitation, inhibiting the growth of undesired tissue or malignant cells, inhibiting inappropriate angiogenesis (neovascularization), limiting tissue damage caused by chronic inflammation, inhibition of tumor cell growth, and the like. The precise effective amount for a subject will depend upon the subject's size and health, the nature and severity of the condition to be treated, and the like. Thus, it is not possible to specify an exact effective amount in advance. However, the effective amount for a given situation can be determined by routine experimentation based on the information provided herein.

The term "pharmaceutically acceptable" refers to compounds and compositions which may be administered to mammals without undue toxicity. Exemplary pharmaceutically acceptable salts include mineral acid salts such as hydrochlorides, hydrobromides, phosphates, sulfates, and the like; and the salts of organic acids such as acetates, propionates, malonates, benzoates, and the like.

The antiangiogenic polypeptide of the invention is administered orally, topically, or by parenteral means, including subcutaneous and intramuscular injection, implantation of sustained release depots, intravenous injection, intranasal administration, and the like. Accordingly, antiangiogenic polypeptides of the invention are preferably administered as a pharmaceutical composition comprising an antiangiogenic polypeptides of the invention in combination with a pharmaceutically acceptable carrier. Such compositions may be aqueous solutions, emulsions, creams, ointments, suspensions, gels, liposomal suspensions, and the like. Suitable carriers (excipients) include water, saline, Ringer'solution, dextrose solution, and solutions of ethanol, glucose, sucrose, dextran, mannose, mannitol, sorbitol, polyethylene glycol (PEG), phosphate, acetate, gelatin, collagen, Carbopol®, vegetable oils, and the like. One may additionally include suitable preservatives, stabilizers, antioxidants, antimicrobials, and buffering agents, for example, BHA, BHT, citric acid, ascorbic acid, tetracycline, and the like. Cream or ointment bases useful in formulation include lanolin, Silvadene® (Marion), Aquaphor® (Duke Laboratories), and the like. Other topical formulations include aerosols, bandages, and other wound dressings. Alternatively one may incorporate or encapsulate the therapeutic compound of the invention in a suitable polymer matrix or membrane, thus providing a sustained-release delivery device suitable for implantation near the site to be treated locally. Other devices include indwelling catheters and devices such as the Alzet® minipump. Ophthalmic preparations may be formulated using commercially available vehicles such as Sorbi-care® (Allergan), Neodecadron® (Merck, Sharp & Dohme), Lacrilube®, and the like, or may employ topical preparations such as that described in U.S. Pat. No. 5,124,155, incorporated herein by reference. Further, one may provide the therapeutic compound of the invention in solid form, especially as a lyophilized powder. Lyophilized formulations typically contain stabilizing and bulking agents, for example human serum albumin, sucrose, mannitol, and the like. A thorough discussion of pharmaceutically acceptable excipients is available in Remington's Pharmaceutical Sciences (Mack Pub. Co.).

The invention also contemplates an article of manufacture which is a labeled container for providing the antiangiogenic polypeptide of the invention. An article of manufacture comprises packaging material and a pharmaceutical agent contained within the packaging material.

The pharmaceutical agent in an article of manufacture is any of the compositions of the present invention suitable for providing the antiangiogenic polypeptide and formulated into a pharmaceutically acceptable form as described herein according to the disclosed indications. Thus, the composition can comprise the antiangiogenic polypeptide or a nucleic acid which is capable of expressing the polypeptide.

The article of manufacture contains an amount of pharmaceutical agent sufficient for use in treating a condition indicated herein, either in unit or multiple dosages.

The packaging material comprises a label which indicates the use of the pharmaceutical agent contained therein, e.g., for treating conditions assisted by the inhibition of angiogenesis, and the like conditions disclosed herein The label can further include instructions for use and related information as may be required for marketing. The packaging material can include container(s) for storage of the pharmaceutical agent.

As used herein, the term packaging material refers to a material such as glass, plastic, paper, foil, and the like capable of holding within fixed means a pharmaceutical agent. Thus, for example, the packaging material can be plastic or glass vials, laminated envelopes and the like containers used to contain a pharmaceutical composition including the pharmaceutical agent.

In preferred embodiments, the packaging material includes a label that is a tangible expression describing the contents of the article of manufacture and the use of the pharmaceutical agent contained therein.

A DNA encoding the antiangiogenic polypeptide of the invention can be used in the form of gene therapy and delivered to a host by any method known to those of skill in the art to treat disorders associated with angiogenic or tissue remodeling-associated conditions.

A preferred embodiment of the present invention relates to methods of inhibiting angiogenesis of solid tumors to prevent further tumor growth and eventual metastasis. To this end, any solid tumor or the region surrounding the tumor accessible to gene transfer will be a target for the disclosed therapeutic applications. A DNA encoding an angiogenic polypeptide, housed within a recombinant viral- or non-viral-based gene transfer system may be directed to target cells within proximity of the tumor by any number of procedures known in the art, including but not limited to (a) surgical procedures coupled with administration of an effective amount of the DNA to the site in and around the tumor (involving initial removal of a portion or the entire tumor, if possible); (b) injection of the gene transfer vehicle directly into or adjacent to the site of the tumor; and, (c) localized or systemic delivery of the gene transfer vector and/or gene product using techniques known in the art.

Any solid tumor that contains angiogenic protein expressing cells will be a potential target for treatment. Examples, but by no means listed as a limitation, of solid tumors which will be particularly vulnerable to gene therapy applications are (a) neoplasms of the central nervous system such as, but again not necessarily limited to glioblastomas, astrocytomas, neuroblastomas, meningiomas, ependymomas; (b) cancers of hormone-dependent, tissues such as prostate, testicles, uterus, cervix, ovary, mammary carcinomas including but not limited to carcinoma in situ, medullary carcinoma, tubular carcinoma, invasive (infiltrating) carcinomas and mucinous carcinomas; (c) melanomas, including but not limited to cutaneous and ocular melanomas; (d) cancers of the lung which at least include squamous cell carcinoma, spindle carcinoma, small cell carcinoma, adenocarcinoma and large cell carcinoma; and (e) cancers of the gastrointestinal system such as esophageal, stomach, small intestine, colon, colorectal, rectal and anal region which at least include adenocarcinomas of the large bowel.

Inhibition of angiogenesis would also be beneficial in disease states characterized by pathological angiogenesis, such as diabetic retinopathy, vascular restenosis, primary pulmonary hypertension, hereditary hemorrhagic telangiectasis, post-operative adhesion formation, atherosclerosis, psoriasis and rheumatoid arthritis.

A DNA fragment encoding the antiangiogenic polypeptide of the invention may be delivered either systemically or to target cells in the proximity of a solid tumor of the mammalian host by viral or non-viral based methods. Viral vector systems which may be utilized in the present invention include, but are not limited to, (a) adenovirus vectors; (b) retrovirus vectors; (c) adeno-associated virus vectors; (d) herpes simplex virus vectors; (e) SV 40 vectors; (f) polyoma virus vectors; (g) papilloma virus vectors; (h) picornavirus vectors; and (i) vaccinia virus vectors.

The recombinant virus or vector containing the DNA encoding the antiangiogenic polypeptide of the present invention is preferably administered to the host by direct injection into a solid tumor and/or quiescent tissue proximal to the solid tumor, such as adipose or muscle tissue. It will, of course, be useful to transfect tumor cells in the region of targeted adipose and muscle tissue. Transient expression of the antiangiogenic polypeptide in these surrounding cells will result in a local extracellular increase in these proteins.

Non-viral vectors which are also suitable include DNA-lipid complexes, for example liposome-mediated or ligand/poly-L-Lysine conjugates, such as asialoglyco-protein-mediated delivery systems (see, e.g., Felgner et al., 1994, J. Biol. Chem. 269: 2550-2561; Derossi et al., 1995, Restor. Neurol. Neuros. 8: 7-10; and Abcallah et al., 1995, Biol. Cell 85:1-7). Direct injection of "naked" DNA may also be used.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The references cited throughout this application are herein incorporated by reference.

The present invention is further illustrated by the following Examples. These Examples are provided to aid in the understanding of the invention and are not construed as a limitation thereof.

EXAMPLE

Experimental Procedures

Cloning and Expression of hTIMP-2 and hTIMP-2 Domains

Human TIMP-2 was cloned via PCR of a human fetal heart cDNA library (Clontech, Palo Alto, Calif.) using primers specific for the mature form of TIMP-2. Two separate TIMP-2 domains were produced using PCR primers designed to yield two fragments of TIMP-2 which encode for either the three N-terminal loops (T2N) or the three C-terminal loops (T2C). A fourth construct, designated EA-T2N, was designed to produce an inactive mutant of T2N using PCR to add two amino acid residues, EA, to the N-terminus of T2N. The full-length TIMP-2 PCR product, as well as the two TIMP-2 fragments and the mutant EA-T2N, were sub-cloned into the yeast expression vector pPICZαA (Invitrogen) and their sequences verified. C-terminal His-tags were designed into each of the constructs to aid in the purification of expressed proteins. Linearized vectors were electroporated into the methylotrophic yeast *Pichia pastoris* for expression (Invitrogen), and integrants were selected by culturing on YPDS (2% peptone, 1% yeast extract, 2% glucose, 1M sorbitol, 2% agar) plates with 100 μg/ml Zeocin (Invitrogen) for three days. Successful insertion of the genes of interest into the *Pichia* genome was verified by PCR using *Pichia*-specific primers, which also verified that recombination occurred at the proper site such that expression of the gene of interest is under the control of the methanol-inducible AOX1 promoter.

Four *Pichia* clones for each gene of interest were tested for expression levels, and the clone expressing the highest amount of each protein was chosen for subsequent studies. Protein identities were verified by N-terminal sequencing. Expression conditions were as follows: 25 ml overnight cultures were grown at 30° C. in BMGY media (2% peptone, 1% yeast extract, 100 mM potassium phosphate pH 6.0, 1.34% yeast nitrogenous base, 1% glucose) containing 100 μg/ml Zeocin and cell pellets were collected the next day by centrifugation at 1500 g. Cultures were induced by re-suspending the cell pellets in 250 ml of methanol-containing media (BMMY: 2% peptone, 1% yeast extract, 100 mM potassium phosphate pH 6.0, 1.34% yeast nitrogenous base, 1% methanol), and allowed to grow for 24 hours. Media containing the secreted expressed protein was cleared of cell content by centrifugation at 3000 g.

Purification of Recombinant TIMP-2 and TIMP-2 Domains

Expressed proteins were initially purified from the yeast media using histidine-affinity binding to a Ni-NTA Agarose resin (Qiagen, Valencia, Calif.) under native conditions. Briefly, expressed protein in 250 ml of cleared media was allowed to bind to 5 ml of resin by nutating for 1 hour at 4° C., and then centrifuged at low speed to collect the resin. Resin carrying the expressed protein was then loaded into a 12 ml BioRad (Hercules, Calif.) glass column by gravity, and the resin was washed with 15 ml of buffer containing 10 mM Imidazole (50 mM $NaH_2PO_4$ pH 8.0, 300 mM NaCl, 10 mM Imidazole) to reduce non-specific binding. Protein was then eluted using 10 ml elution buffer containing 100 mM Imidazole (50 mM $NaH_2PO_4$ pH 8.0, 300 mM NaCl, 100 mM Imidazole), and concentrated by centrifugation using membrane concentrators with 3 kDa molecular weight cutoff (Centriprep, Amicon). Concentrated protein was further purified to homogeneity by C4 Reverse Phase HPLC. Separation was carried out over a gradient, from 100% Buffer A (0.05% trifluoroacetic acid in water) to 60% Buffer B (0.05% trifluoroacetic acid in acetonitrile) in 60 minutes at a flow rate of 1 ml per minute. Fractions containing the peak of interest were then dialyzed versus $ddH_2O$ to remove salts and acetonitrile. Purity was confirmed by silver staining of SDS-Page gels and/or amino acid composition. Protein was lyophilized and stored at −20° C. until needed and then reconstituted in the appropriate assay buffer.

SDS-Page Electrophoresis and Protein Sequencing

Proteins were resolved on 12% NuPage gels (Invitrogen) ran at 200V for one hour and visualized either by silver stain or coomassie. Proteins to be sequenced were blotted onto PVDF using a BioRad Transblot Apparatus for one hour at 100V, stained with amido black, and excised from the membrane. N-terminal sequence was determined by Edman degradation using an Applied Biosystems 477A Protein Sequencer (Dana Farber Microsequencing Facility, Boston, Mass.).

Peptide Synthesis and Purification

Peptide sequences were designed to represent various smaller structural domains of the carboxy-terminus of TIMP-2 These include: a 10 amino acid peptide corresponding to Loop 5 with sequence TRCPMIPCYI (SEQ ID NO: 2), a 24 amino acid peptide corresponding to Loop 6 with sequence ECLWMDWVTEKNINGHQAKFFACI (SEQ ID NO: 1), and a 19 amino acid peptide corresponding to the carboxy-terminal tail with sequence AWYRGAAPPKQE-FLDIEDP (SEQ ID NO: 3). A fourth peptide of sequence VIRAK (SEQ ID NO: 4) corresponding to a conserved sequence in the N-terminal domain of all TIMPs was also synthesized for use as a control peptide. All four peptides were synthesized via Fmoc solid phase synthesis on chlorotrityl resins using DIC/HBTU/HOBT activation on Advanced Chemtech 396-5000 multiple peptide synthesizers (ACT, Louisville, Ky.) to yield peptides as a trifluoroacetic acid salt. Synthesis was performed at ResGen, Invitrogen Corporation (Huntsville, Ala.). Synthetic peptides were further purified by us using C18 Reverse Phase HPLC to remove any truncation products. Briefly, 1 mg of lyophilized peptide was re-suspended in 1 ml of Buffer A (0.05% trifluoroacetic acid in water), and loaded onto the column. Separation was carried out over a gradient, from 100% Buffer A to 60% Buffer B (0.05% trifluoroacetic acid in acetonitrile) in 60 minutes at a flow rate of 1 ml per minute. Fractions containing the peak of interest were collected by hand, and subjected to Mass Spec analysis to confirm identity and purity and to determine yield. Purified peptides were lyophilized using a Savant speed vac and then stored at −20° C.

MMP-Inhibitory Activity

MMP-inhibitory activity was assessed using a quantitative $^{14}$C-Collagen Film Assay, as previously described by us (Moses et al., 1990). Briefly, $^{14}$C-labeled collagen was added to 96 well plates and allowed to polymerize. To determine inhibitory activity, wells were treated with a known amount of activated type I collagenase plus test sample or with collagenase alone, and the plates incubated at 37° C. for 2.5 hours to allow for release of $^{14}$C by the enzyme. Supernantants were then analyzed in a Wallac Scintillation Counter, and percent inhibition of collagenolytic activity was calculated. An $IC_{50}$ was defined as the amount of protein necessary to inhibit the proteolytic activity of collagenase by 50%.

Cell Culture and Capillary Endothelial Cell Proliferation

Capillary endothelial cells (EC), isolated from bovine adrenal cortex, were a kind gift of Dr. Judah Folkman (Children's Hospital, Boston) and were maintained in DMEM (Gibco) supplemented with 10% calf serum (HyClone) and 3 ng/ml bFGF, and grown at 37° C. in 10% $CO_2$. Capillary EC proliferation was measured as previously reported by us (Moses et al., 1990; Moses et al., 1992; O'Reilly et al., 1994; Moses et al., 1999) using a modification of the method of Connolly and coworkers (and verified by cell counting using a Coulter Counter) (Connolly et al., 1986). Briefly, capillary EC were plated on pre-gelatinized 96 well plates at a density of 2,000 cells per well in DMEM supplemented with 5% calf serum and allowed to attach for 24 hours. The next day, cells were treated with fresh media with or without 1 ng/ml bFGF and challenged with the test proteins at various concentrations. All samples were tested in duplicate. Control wells contained cell treated with media alone or media with bFGF. After 72 hours, the media was removed and the cells were lysed in buffer containing Triton X-100 and the phosphatase substrate p-nitrophenyl phosphate. After a two-hour incubation at 37° C., NaOH was added to each well to terminate the reaction and cell density was determined by calorimetric analysis using a SpectraMax 190 multiwell plate reader (Molecular Devices).

Chick Chorioallantoic Membrane Assay (CAM)

The chick CAM assay was conducted as previously reported by us (Moses et al., 1990; Moses et al., 1992; O'Reilly et al., 1994; Moses et al., 1999; Fang et al., 2000) Briefly, three day old chick embryos were removed from their shells and incubated in plastic Petri dishes for three days. On embryonic day 6, samples and controls mixed into methylcellulose discs were applied to the surfaces of developing CAMs, above the dense subectodermal plexus. After 48 hours of incubation, the eggs were examined for vascular reactions under a dissecting scope (60×) and photographed. All determinations were made by 3 independent members of the laboratory, in a double-blinded fashion.

Mouse Corneal Pocket Assay

In vivo inhibition of angiogenesis was also tested using the mouse corneal pocket assay as previously described (O'Reilly et al., 1994; Moses et al., 1999). Hydron pellets containing sucrose octasulfate and, either test sample (5 μg) plus bFGF (40 ng/ml) or bFGF (40 ng/ml) alone were implanted into corneal micropockets of C57BI/6. Each animal carried a pellet containing the test sample plus bFGF in one eye, and a control bFGF pellet in the contralateral eye. After six days, angiogenesis was evaluated using a slit lamp microscope, and each eye was photographed. The area of neovascularization for each cornea was calculated from the length of the vessels (VL) invading the cornea as well as the clock hours (CH) covered as described by the formula VL×CH×0.0628.

Apoptosis Assay

In situ detection of cell death was determined using terminal deoxynucleotidyl transferase dUTP nick-end labeling (TUNEL) following manufacturer's instructions (In Situ Cell Death Detection Kit, Roche Applied Science, Indianapolis, Ind.). Capillary EC were plated at a density of 10,000 cells per well on pre-gelatinized Lab-Tek Chamber Slides (Nalge Nunc, Naperville, Ill.) in DMEM supplemented with 5% calf serum and allowed to attach for 24 hours. The next day, cells were treated with fresh media supplemented with 1 ng/ml bFGF and challenged with an $IC_{50}$ dose of Loop 6 or 100 mM wortmannin, a dose previously reported to induce apoptosis of capillary E (Flusberg et al., 2001). Cells stimulated with bFGF alone were also used as controls. All samples were tested in duplicate. After 6 hours, the cells were rinsed with PBS and then fixed in 4% paraformaldehyde for 1 hour at room temperature. Fixed cells were again rinsed with PBS and permeabilised with 0.1% Triton X-100 in 0.1% sodium citrate on ice for 2 minutes. After two more rinses in PBS, the cells were exposed to TUNEL reaction mixture and incubated at 37° C. After 1 hour, cells were then incubated with 1 μg/ml 4,6-diamidino-2-phenylindole (DAPI) at room temperature for 30 minutes, rinsed in PBS and mounted using Fluoromount G (Southern Biotechnology Associates, Birmingham, Ala.). Apoptotic nuclei were detected using a Nikon Eclipse TE300 microscope (Nikon Instruments, Melville, N.Y.).

Cell Cycle Analysis

Capillary EC were plated at a density of 100,000 cells per plate unto pre-gelatinized 60 mm dishes in DMEM supplemented with 5% calf serum and allowed to attach overnight. The next day, the media was replaced with DMEM supplemented with 0.4% calf serum in order to synchronize the cells by serum starvation. After 36 hours, synchronized cells were stimulated with DMEM containing 5% calf serum plus 1 ng/ml bFGF, and then treated with an $IC_{50}$ dose of Loop 6 or an equivalent dose of the T2-Tail peptide as control. After 16 hours, the cells were rinsed with PBS, trypsinized and collected by centrifugation. Pelleted cells were rinsed again with PBS and resuspended in 1 ml of 80% ethanol in PBS, and stored at −20° C. overnight. The next morning, cells were collected by centrifugation and resuspended in 500 μl of staining solution (0.1% sodium citrate, 100 μg/ml RNAse A, 0.1% Nonidet-P40, 50 μg/ml propidium iodide). After 30 minutes, DNA content of the cells and the percentages of cells in the various stages of the cell cycle were determined using a FACSVantage SE (Becton Dickinson, Franklin Lanes, N.J.). FACS analysis was performed at the Howard Hughes Institute of Medicine FACS Core Facility at Children's Hospital. All samples were tested in at least duplicate. Histograms of representative experiments for each test condition were created using WinMDI 2.8 (The Scripps Research Institute, La Jolla, Calif.).

Immunoblot Analyses

Western analyses of capillary EC lysates were performed as previously described by us (Moses et al., 1999; Yan et al., 2001). Capillary EC were plated, synchronized and treated with an IC$_{50}$ dose of Loop 6 as described above for cell cycle analysis. After 16 hours, cells exposed to bFGF alone or bFGF and Loop 6 were rinsed in PBS and lysed directly in the culture dish by addition of 500 µl of lysis buffer (1% SDS in 10 mM Tris-Hcl, pH 7.4). Collected lysates were boiled for 5 minutes, mixed by vortexing and then placed on ice. Samples were repeatedly passed through a 22-gauge syringe needle in order to shear the DNA. The samples were then centrifuged, and the supernatant collected. Protein concentration of the lysates was determined using the MicroBCA method (Pierce, Rockford, Ill.). Equal amounts of protein were loaded unto 12% SDS-PAGE gels under reducing conditions, resolved by electrophoresis and subsequently transferred to nitrocellulose using a TransBlot apparatus (BioRad). Membranes were blocked with 5% low fat dry milk in TBST (10 mM Tris, pH 7.2, 50 mM NaCl, 0.5% Tween 20) overnight at 4° C. and then probed for 1 hour at room temperature with antibodies to various cell cycle associated proteins, including: Cyclin D1 (Pharmingen, BD Biosciences, Palo Alto, Calif.), Cyclin E (Pharmingen), Cyclin A (Santa Cruz Biotechnology, Santa Cruz, Calif.) and p27 (Santa Cruz). Blots were washed three times with TBST and then incubated with a 1:5000 dilution of either mouse or rabbit horseradish peroxidase conjugated secondary antibodies (Sigma, St. Louis, Mo.) for 30 minutes at room temperature. Labeled proteins were detected using Supersignal West Pico Chemiluminescence Substrate (Pierce).

Results

Expression of TIMP-2 and TIMP-2 Domains

Figure 2A:
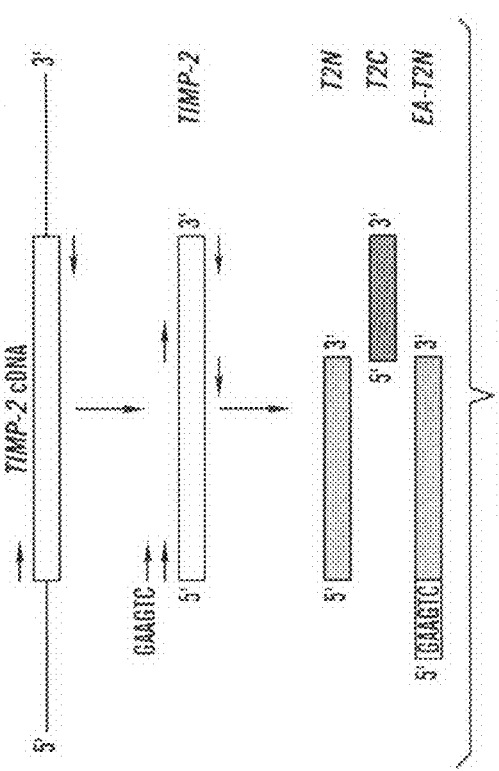
Figure 2D:
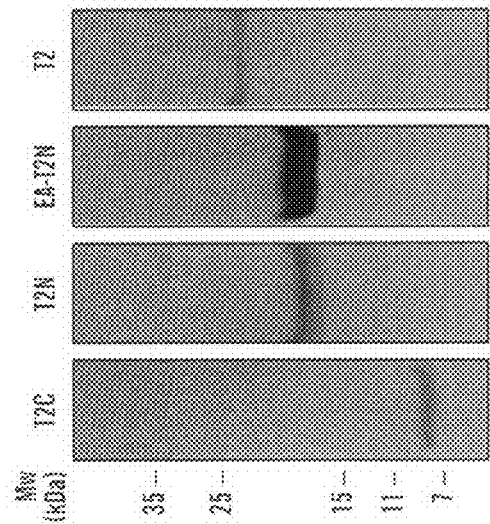
Figure 2C:
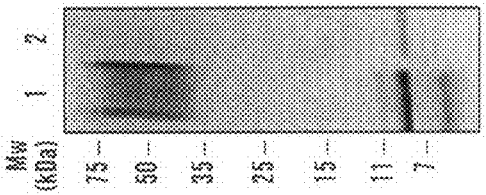

Human TIMP-2 was first cloned from a human heart cDNA library using high-fidelity PCR and primers designed to produce full-length TIMP-2, a 3'-deletion fragment and a 5'-deletion fragment (FIG. 2A). Cloning of these gene fragments result in the expression of two domains of TIMP-2 as distinct proteins. The first is composed of the three N-terminal disulfide-bonded loops (~15 kD) designated T2N, and the second is composed of the three C-terminal disulfide-bonded loops (~8.5 kD) designated T2C. In addition, a mutant form of T2N that encodes for a form of T2N with additional glutamine and alanine residues at the N-terminus of the protein, and designated EA-T2N, was designed and expressed for use as a control for MMP-inhibition. All proteins, as well as intact human TIMP-2, were expressed using the *Pichia pastoris* yeast expression system, which has been shown to successfully produce other disulfide-bonded proteins (Ikegaya et al., 1997; Sun et al., 1997). Expressed proteins with incorporated C-terminal His-tags are secreted into the growth media and purified to homogeneity by histidine-affinity chromatography followed by C4 Reverse Phase HPLC. A sample chromatogram of the purification of T2C by reverse phase HPLC is shown in FIG. 2B. Sample purity was monitored by SDS-PAGE followed by silver-staining as previously reported (Moses et al., 1990; Moses et al., 1999). FIG. 2C shows a representative example of a silver-stained gel of both the HPLC sample starting material (Lane A) and purified T2C (Lane B). Once purified to homogeneity, identity was verified via N-terminal amino acid sequencing. Typical yields of each sample protein were as follows: 1.2 mg/L for T2N, 240 µg/L for T2C, 15 mg/L for EA-T2N, and 300 µg/L for intact TIMP-2.

T2N, but not T2C, Inhibits Metalloproteinase Activity

Figure 3B:
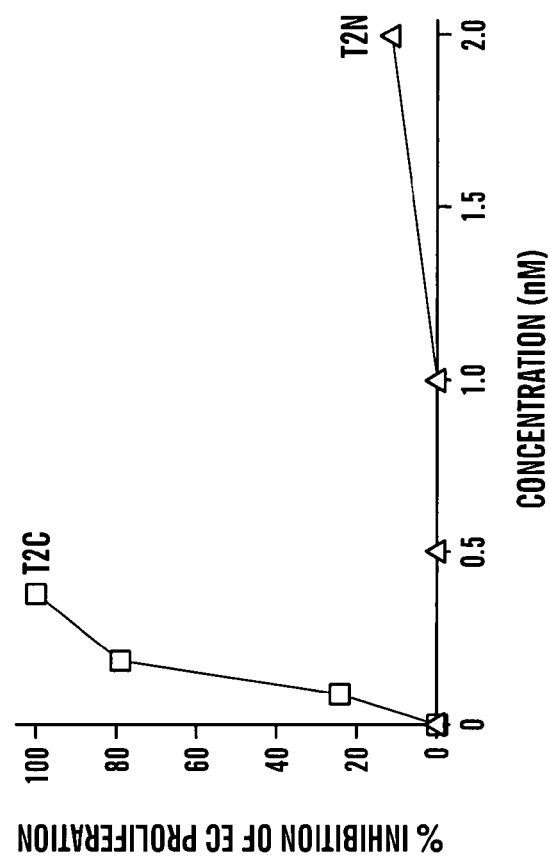
FIGS. 3A and 3B demonstrate uncoupling of the in vitro MMP-inhibitory and anti-proliferative activities of TIMP-2.
Figure 3A:
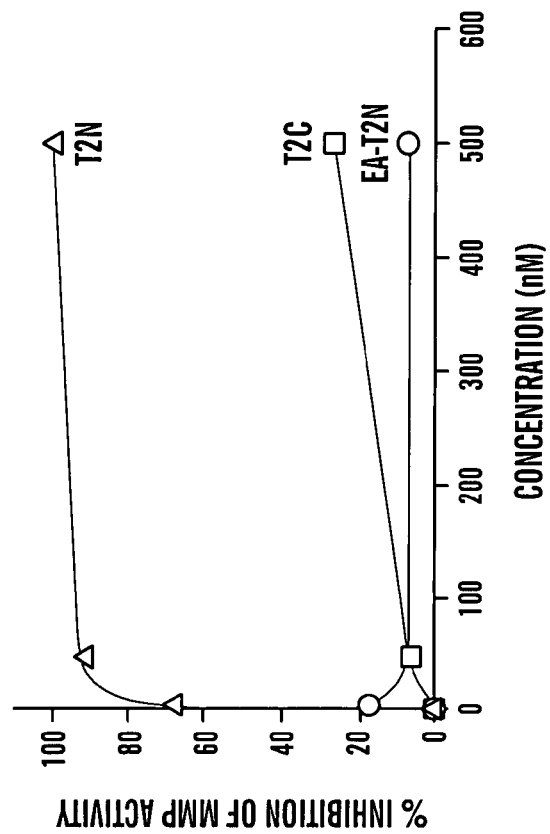

To demonstrate that the N-terminal domain of TIMP-2, T2N, retains MMP-inhibitory activity as previously reported (Murphy et al., 1991; O'Shea et al., 1992; Tolley et al., 1993; Fernandez-Catalan et al., 1998; Muskett et al., 1998; Butler et al., 1999) and to validate the ability of this expression system to produce biologically active protein, we tested TIMP-2, the TIMP-2 domains, and an MMP-inhibition deficient form of T2N, EA-T2N, for their ability to inhibit MMP activity using a standard quantitative radiometric MMP assay (Moses et al., 1990). As expected, T2N inhibited MMP activity at concentrations comparable to intact TIMP-2, with an IC$_{50}$ of approximately 7.5 nM (FIG. 3A). No significant inhibition of MMP activity was detected for either T2C or EAT2N, even at concentrations approximately 100-fold higher than that of the IC$_{50}$ of T2N (FIG. 3A).

T2C, but not T2N, Inhibits the Proliferation of Capillary Endothelial Cells

Since the MMP-inhibitory activity of TIMPs has been attributed to the highly conserved N-terminal portion of the molecules, we hypothesized that the anti-proliferative effect of TIMP-2 on capillary EC resides in the more variable C-terminal domain (FIG. 1). We therefore tested individual TIMP-2 domains for their ability to suppress capillary EC proliferation in vitro and found that T2C alone, inhibited capillary EC proliferation driven by the angiogenic stimulant basic fibroblast growth factor (bFGF) with an IC$_{50}$ of approximately 140 nM (FIG. 3B) and showed no evidence of cytotoxicity. These results are consistent with those previously reported for TIMP-2 (Murphy et al., 1993). Although T2N is responsible for inhibition of MMP activity, it had no significant effect on capillary EC proliferation. These results demonstrate that the inhibitory effect of TIMP-2 on capillary EC proliferation is independent of MMP inhibition, and that these bioactivities can be dissociated from each other. This unique anti-proliferative activity of T2C represents a second anti-angiogenic domain within TIMP-2.

TIMP-2 Domains Independently Inhibit Angiogenesis in Vivo in the Chick Chorioallantoic Membrane (CAM)

Figure 4A:
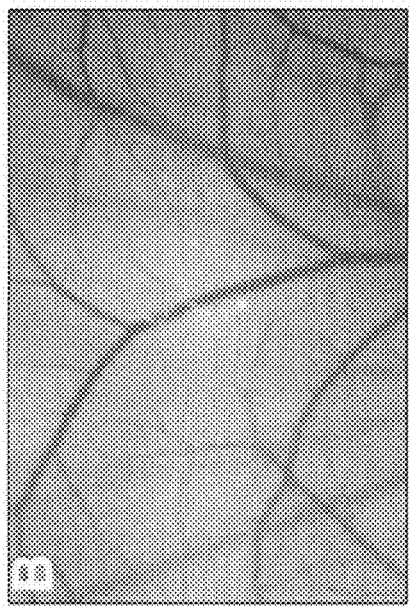
FIGS. 4A to 4D show that TIMP-2 and TIMP-2 domains suppress embryonic angiogenesis in the chick chorioallantoic membrane assay (CAM). Representative CAMs in which equivalent doses of each expressed protein were tested are shown.
Figure 4B:
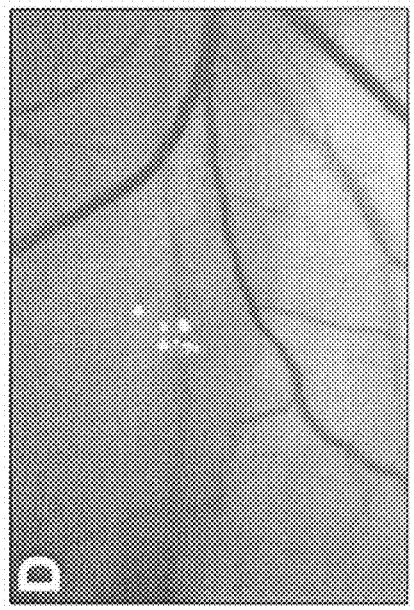
Figure 4C:
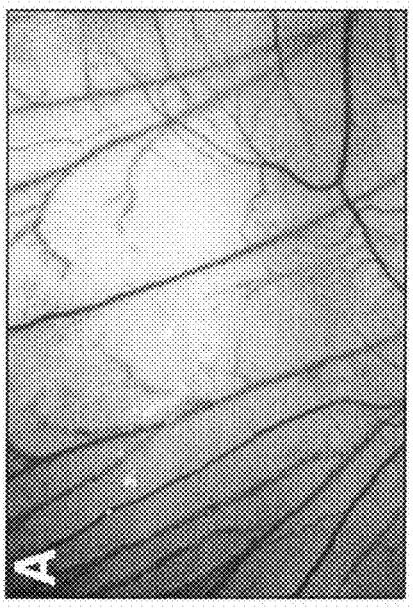
Figure 4D:

Given that MMP inhibitors have been shown to inhibit angiogenesis and that T2C independently inhibits capillary endothelial cell proliferation, we next tested both T2C and T2N for their ability to inhibit embryonic, unstimulated angiogenesis in vivo in the CAM assay. Approximately 120 eggs were tested in these experiments. Representative CAMs for each of the TIMP-2 domains tested are shown in FIG. 4. The CAMs shown were treated with equivalent amounts of each of the proteins tested at the lowest dose in which inhibition should be achieved for T2N. The addition of T2C (FIG. 4A) or T2N (FIG. 4B) to the chorioallantoic membrane resulted in a decrease in neovascularization. T2C produced avascular zones at doses as low as 112 pmol per egg, while T2N inhibited at doses approximately 5 fold higher. EA-T2N, which is deficient in MMP- and capillary EC-inhibitory activity, did not inhibit neovascularization (FIG. 4C). Of particular interest is the fact that, in addition to a difference in the anti-angiogenic potency of T2C and T2N, the appearance of the vasculature in each of these cases differed significantly. CAMs treated with T2C had much larger avascular zones and the few remaining vessels had a tortuous appearance reminiscent of vessels undergoing regression (Burt et al., 1995). The inhibition of neovascularization in the vicinity of the methylcellulose disc containing T2N, however, could be characterized by a dissolution of CAM vessels. Given that numerous studies have demonstrated the requirement for increased MMP activity at the migrating edge of growing vessels during angiogenesis (Monsky et al., 1993; Partridge et al., 1997; Giannelli et al., 1997; Werb, 1997), the appearance of the CAMs treated with T2N is consistent with the direct inhibition of MMPs. The results with T2N are also consistent with those observed for CAMs treated with intact TIMP-2 (FIG. 4D).

T2C Inhibits bFGF-Driven Neovascularization in the Mouse Corneal Pocket Assay

Figure 5:
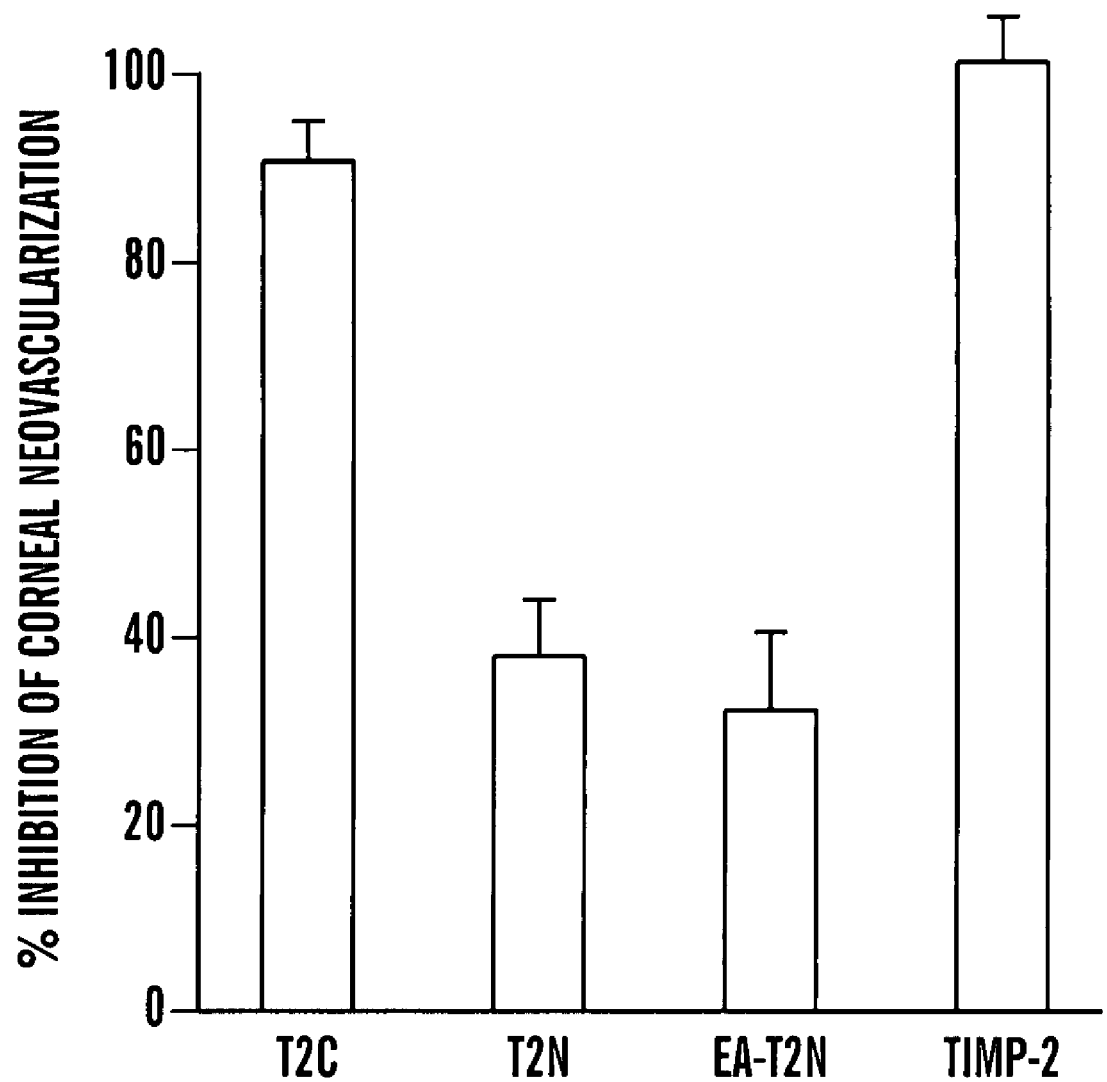
FIG. 5 shows percent inhibition of angiogenic mitogen-stimulated corneal neovascularization in vivo in the mouse corneal pocket assay. Hydron pellets containing either bFGF or bFGF plus test protein, either T2C, T2N, EA-T2N, or intact TIMP-2 were tested in the corneas of C57/B16 mice using a standard protocol. The data represents the average percent inhibition obtained from separate experiments of 18 corneas per treatment group.

We next assessed the ability of T2C to inhibit angiogenesis in a second and more complex in vivo system, the mouse corneal pocket assay, where the neovascularization is stimulated by the addition of an exogenous angiogenic mitogen. T2C (5 µg/eye) resulted in an 87% reduction of bFGF-driven corneal neovascularization when compared to the contralateral control eye treated with only bFGF. Surprisingly, treatment of the corneas with T2N resulted in only modest inhibition of angiogenesis and did not differ significantly from the inhibition observed when corneas were treated with the MMP-inhibition deficient form of T2N, EA-T2N, suggesting that direct inhibition of MMP activity may not be sufficient to inhibit mitogen-driven angiogenesis. As expected, intact TIMP-2 resulted in potent inhibition of corneal neovascularization. These results using intact TIMP-2 show no statistically significant difference from those obtained with T2C. FIG. 5 shows the average percent inhibition obtained from separate experiments of 18 corneas per treatment group.

Loop 6, a 2.9 kDa Domain of T2C, Inhibits Capillary EC Proliferation

Figure 6A:
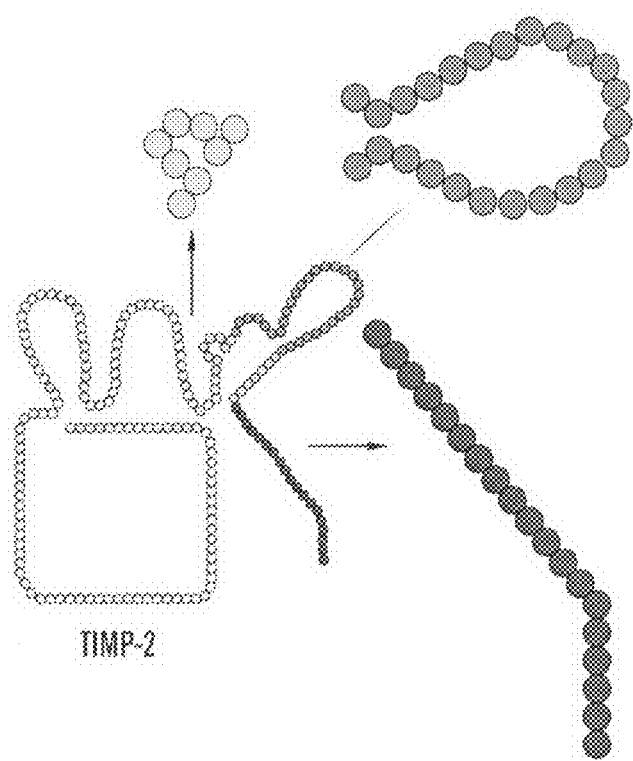
FIGS. 6A to 6C show that loop 6, a 24 amino acid peptide of T2C, inhibits capillary EC proliferation.
Figure 6B:
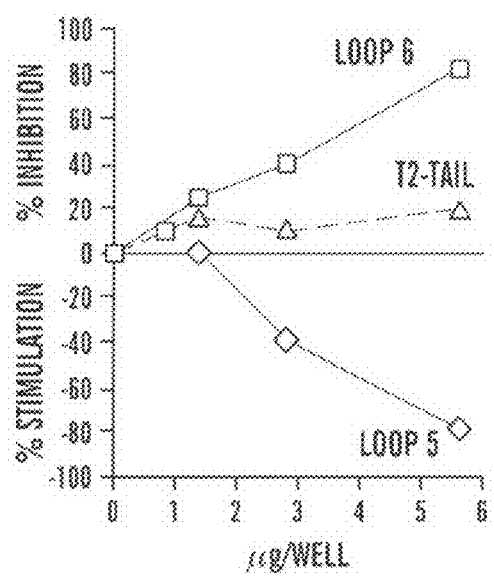
Figure 6C:
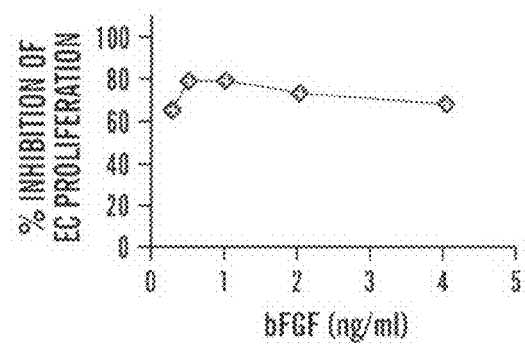

To further map the anti-proliferative activity of TIMP-2 within T2C, three peptides corresponding to various smaller domains of T2C were synthesized, purified and tested for their ability to inhibit bFGF-stimulated capillary EC proliferation in vitro. These domains and are depicted in FIG. 6A. One peptide, corresponding to Loop 6 of intact TIMP-2 with amino acid sequence ECLWMDWVTEKNINGHQAKF-FACI (SEQ ID NO: 1), significantly inhibited capillary EC proliferation, while a peptide corresponding to the carboxy-terminal tail (T2-Tail), AWYRGAAPPKQEFLDIEDP (SEQ ID NO: 3), had no effect. A peptide corresponding to Loop 5 of intact TIMP-2, TRCPMIPCYI (SEQ ID NO: 2), stimulated the proliferation of capillary EC (FIG. 6B). A fourth peptide corresponding to the highly conserved VIRAK (SEQ ID NO:4) sequence of Loop 1 of all four intact TIMPs (amino acid residues 18-22) was used as a random peptide control and resulted in no inhibition of capillary EC proliferation (data not shown). Loop 6 inhibited capillary EC proliferation at doses comparable to intact TIMP-2, suggesting that Loop 6 is responsible for the anti-proliferative activity of intact TIMP-2. Given that Loop 6 inhibits bFGF-driven endothelial cell proliferation, we asked whether Loop 6 could directly compete with bFGF. Capillary EC were treated with increasing concentrations of bFGF in the presence of Loop 6 at a dose which results in an $IC_{50}$, and found that the anti-proliferative effect of Loop 6 is not abrogated by increasing doses of bFGF (FIG. 6C), thus Loop 6 is not a competitor of FGF.

Loop 6 Inhibits Both Physiologic and Mitogen-Driven Angiogenesis in Vivo

To determine whether the in vivo anti-angiogenic activity of T2C is also retained within Loop 6, we tested Loop 6 in the chick chorioallantoic membrane assay. Other synthetic peptides to Loop 5 and to T2-Tail were used as controls. Loop 6 resulted in avascular zones at doses comparable to those tested for T2C (FIG. 7A and FIG. 7B). Neither Loop 5 nor the T2-Tail peptides had any significant effect on neovascularization (data not shown). Interestingly, although Loop 5 stimulated the proliferation of capillary EC in vitro, this effect did not translate into the stimulation of neovascularization in vivo in this model.

We next tested Loop 6 in the mouse corneal pocket assay to determine whether this peptide alone could also inhibit mitogen-driven angiogenesis in vivo. Corneas treated with Loop 6 (3 µg/eye) showed a significant suppression (~80%) of bFGF-stimulated neovascularization when compared to the contralateral control eyes. These results are comparable to those obtained for intact TIMP-2 and T2C. As with T2C, the density of the vessels around the limbus of the corneas was also markedly decreased (FIG. 7C). These results are significant because they demonstrate that the anti-proliferative activity of Loop 6 within TIMP-2 is independent of MMP inhibitory activity and that it is a powerful inhibitor of bFGF-mediated angiogenesis in vivo. The 2.9 kD Loop 6 therefore, represents a novel, potent, small molecular weight inhibitor of angiogenesis.

Loop 6 Inhibits Cell Cycle Progression and Does Not Induce Apoptosis of Capillary EC We next examined whether the anti-angiogenic effects of Loop 6 were due to induction of apoptosis in capillary endothelial cells. bFGF-stimulated capillary EC were treated with the $IC_{50}$ dose of Loop 6 for 6 hours and apoptotic nuclei were detected using terminal deoxynucleotidyl transaferase dUTP nick-end labeling (TUNEL) as well as 4,6-diamidino-2-phenylindole (DAPI) staining. No apoptotic nuclei were observed in the bFGF treated control cells nor in Loop 6 treated capillary EC indicating that Loop 6 is not an inducer of apoptosis. Wortmannin, which has previously been shown to induce apoptosis of capillary EC (Flusberg et al., 2001), was used as a positive control and showed the expected apoptosis. All experiments were performed in duplicate.

Figures 8A, 8B:
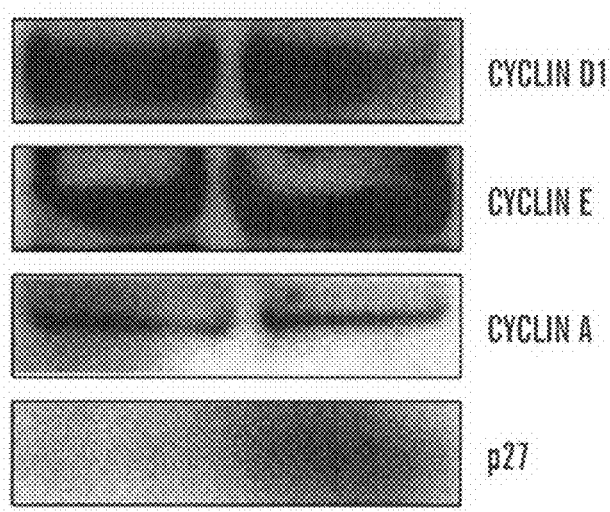
FIGS. 8A and 8B show that loop 6 inhibits cell cycle progression via increased levels of p27.

To determine whether the anti-proliferative effect of Loop 6 on capillary EC is due to the inhibition of cell cycle progression, capillary EC were synchronized by serum starvation and then stimulated with bFGF and treated with an $IC_{50}$ dose of Loop 6 or an equivalent dose of the T2-Tail peptide, which did not inhibit capillary EC proliferation, as a negative control. After 16 hours, cells were trypsinized, fixed in ethanol, stained with propidium iodine and analyzed by flow cytometry for DNA content. Cells treated with Loop 6 showed a marked reduction in the number of cells in G2/M as compared to bFGF controls or cells treated with T2-Tail peptide (9.53%, 39.7% and 34.6%, respectively) as well as an increase in the number of cells in G1 (45.6%, 26.8% and 27.8%, respectively). However, the number of cells in S-phase did not change significantly, suggesting that Loop 6 may suppress S-phase transition. These results are consistent with those previously reported for microvascular endothelial cells engineered to overexpress protein kinase Cδ in which a block of S-phase transition was observed (Ashton et al., 1999). The percentage of cells in each of the various stages of the cell cycle are shown in FIG. 8A.

Loop 6 Inhibition of Cell Cycle Progression is Associated with Increased Levels of p27

We next examined whether the inhibitory effects of Loop 6 on cell cycle progression were the result of altered levels of various positive and negative regulators of cell cycle. Lysates from cells treated with Loop 6 and control lysates from bFGF stimulated capillary EC were resolved by SDS-PAGE and analyzed by western blotting using antibodies to various cell cycle associated proteins. No significant differences were observed in the levels of Cyclins D1, E or A (FIG. 8B). Interestingly, p27, a negative regulator of cell cycle progression, was found to be significantly increased in cells treated with Loop 6 (FIG. 8B). Previous studies have shown that overexpression of p27 in endothelial cells results in a block in cell cycle progression (Goukassian et al., 2001), and that the cellshape-dependent inhibition of capillary EC proliferation is associated with a failure to down-regulate p27 (Huang et al., 1998). Ashton and coworkers have also shown that the anti-proliferative effect of protein kinase Cδ on endothelial cells is the result of increased levels of p27 despite a lack of change in the levels of Cyclins D1, E, and A (Ashton et al., 1999).

Discussion

It is widely appreciated that TIMPs are multi-functional proteins with respect to cell growth, apoptosis, angiogenesis and other bioactivities (Brew et al., 2000; Baker et al., 2002). Although some of these differences in TIMP activities can be attributed to differences in their affinity for various MMPs and/or their role in MMP activation, other functions appear to be entirely MMP-independent. For example, both TIMP-1 and TIMP-2 have been shown to possess erythroid-potentiating activity (Gasson et al., 1985; Stetler-Stevenson et al., 1992). TIMP-3 has been reported to inhibit tumor necrosis factor-alpha converting enzyme (Amour et al., 1998) as well as inducing apoptosis (Smith et al., 1997; Baker et al., 1999; Bond et al., 2000), while TIMP-1 actually inhibits apoptosis (Guedez et al., 1998b; Guedez et al., 1998a; Li et al., 1999). TIMP-2 has been shown to induce apoptosis in some systems (Lim et al., 1999; Brand et al., 2000) but to have no effect in others (Bond et al., 2000). Of particular interest is the fact that only TIMP-2 has been shown to inhibit capillary EC proliferation (Murphy et al., 1993; Anand-Apte et al., 1997).

Given that all TIMPs can inhibit MMP activity, the ability of TIMP-2 to inhibit capillary EC proliferation has been suggested to constitute a second function of TIMP-2, independent of its MMP-inhibitory activity (Murphy et al., 1993; Hoegy et al., 2001). Based on these findings, we hypothesized that there must be a structural entity unique to TIMP-2 that might be responsible for the inhibition of mitogen-driven capillary EC proliferation, thereby representing a second anti-angiogenic site within the molecule. In fact, a mutant form of TIMP-2 that lacks MMP-inhibitory activity has recently been shown to inhibit the proliferation of various tumor cell lines (Hoegy et al., 2001). However, no direct evidence of independent structural elements responsible for growth inhibition has been demonstrated prior to this current study (Murphy et al., 1993; Hayakawa et al., 1994; Hoegy et al., 2001). In our structure-function study, we isolate and characterize the MMP-dependent and MMP-independent anti-angiogenic effects of TIMP-2 and demonstrate, for the first time, that these activities are structurally independent. In doing so, we have identified a novel inhibitor of angiogenesis, Loop 6.

Our first series of experiments demonstrate that TIMP-2 possesses two anti-angiogenic activities, one that is associated with MMP inhibition (T2N) and one that is not (T2C). These in vitro studies showed that the MMP-inhibitory deficient T2C is responsible for the unique ability of TIMP-2 to inhibit capillary EC proliferation. T2C inhibited angiogenesis in both the chorioallantoic membrane assay (FIG. 4B) and in the mouse corneal pocket assay (FIG. 5). The level of inhibition is comparable to that obtained with intact TIMP-2 suggesting that we have indeed isolated the growth-inhibitory site of TIMP-2. We further mapped the anti-proliferative activity of T2C to the 24 amino acid sequence of Loop 6 (FIG. 6B). Importantly, as with T2C, Loop 6 significantly inhibited angiogenesis in two different models, the CAM and the mouse corneal pocket assay (FIG. 7). It is interesting to note that the morphology of the few remaining vessels in the CAMs treated with either T2C or Loop 6 was dramatically different than those in the CAMs treated with intact TIMP-2, in that the vessels in the vicinity of the methylcellulose disc containing T2C or Loop 6 had a tortuous appearance and resembled vessels undergoing regression, while the CAMs treated with intact TIMP-2 were characterized by an apparent dissolution of the vessels (FIG. 4 and FIG. 7) (Burt et al., 1995).

Given that neither T2C nor Loop 6 inhibit MMP activity, our results demonstrate that TIMP-2 has an anti-angiogenic domain that is independent of direct MMP inhibition. Interestingly, a recent study has found that T2C can inhibit the activation of pro-MMP-2 presumably by sequestering pro-MMP-2 away from the activating complex (Kai et al., 2002). However, this study also demonstrates that the binding of T2C to pro-MMP-2 occurs at the carboxy-terminal tail of TIMP-2 (T2-Tail) and that these specific interactions with the PEX domain of MMP-2 are required for cell surface activation of pro-MMP-2. In fact, Kai and coworkers show that a protein comprised of Loops 4 through 6 of TIMP-2 but having the carboxy-terminal tail of TIMP-4 was unable to facilitate the activation of pro MMP-2. These findings, along with our own, demonstrate that the ability of TIMP-2 to inhibit capillary EC proliferation, which we have isolated to Loop 6 alone, is not only independent of its ability to directly inhibit MMP activity, but is also most likely to be independent of its involvement in pro-MMP activation.

In fact, our results demonstrate that the anti-proliferative effect of Loop 6 is due, at least in part, to its ability to block cell cycle progression and not to the induction of apoptosis (FIG. 8). In addition, our results show that the inhibition of cell cycle progression by Loop 6 is associated with increased levels of p27. These findings are not without precedent in that other inhibitors of endothelial cell proliferation have been shown to increase the level of p27 (Huang et al., 1998; Ashton et al., 1999; Goukassian et al., 2001). Our results are particularly significant, however, in that no TIMP, or fragment of any TIMP, has yet been shown to directly inhibit cell cycle progression. Interestingly, Loop 6 did not inhibit the proliferation of vascular smooth muscle cells (data not shown), suggesting that the inhibitory effects of Loop 6 are specific to endothelial cells.

The in vivo angiogenesis studies conducted in this report also reveal important differences in the types of angiogenesis inhibition effected by different domains of TIMP-2. Although the MMP-inhibitory domain, T2N, suppressed embryonic neovascularization, presumably via anti-metalloproteinase activity, this same domain did not suppress the mitogen-stimulated corneal neovascularization that most closely mimics aberrant angiogenesis in vivo. In order to determine the role of MMP inhibition alone on these two types of in vivo angiogenesis, we complimented our T2N studies by designing an MMP-inhibitory deficient protein in the form of EA-T2N based on recent studies demonstrating that the additional of amino acids at the N-terminus of TIMP-2 resulted in the abrogation of MMP-inhibitory activity (Wingfield et al., 1999). EA-T2N did not inhibit MMP activity and did not inhibit embryonic angiogenesis in the CAM assay (FIG. 4A). In fact, although T2N resulted in, at best, modest inhibition of angiogenesis (FIG. 5) in the mouse corneal pocket assay, in which neovascularization is stimulated by an angiogenic mitogen, these results are not statistically different from those observed with EA-T2N. In contrast, both the anti-proliferative, anti-angiogenic domain T2C and its smaller peptide, Loop 6, proved to be inhibitors of both embryonic and mitogen-stimulated angiogenesis in vivo.

These data suggest that the inhibition of MMP activity may be sufficient to inhibit physiologic angiogenesis as represented by the embryonic vasculature of the chick chorioallantoic membrane, but alone may not inhibit the neovascularization which is characteristic of pathological conditions. This angio-inhibitory limitation may explain the less than successful results of clinical testing of synthetic MMP inhibitors (Coussens et al., 2002) whose activity is dependent solely on their enzymatic inhibition.

In this study, we identify Loop 6 as a new inhibitor of angiogenesis found within the C-terminus of TIMP-2. Several recently identified angiogenesis inhibitors have been found to be fragments of larger parental proteins that may or may not share the activity of the inhibitor. Cryptic inhibitors of angiogenesis, including endostatin and angiostatin, are housed within proteins that do not, in their intact form, inhibit angiogenesis. Peptide inhibitors of angiogenesis, including the one identified here and others, such as platelet factor 4, thrombospondin and angiotensinogen, share the anti-angiogenic activity of the parent protein. It is also now widely appreciated that small molecular weight inhibitors such as Loop 6 may exhibit more desirable therapeutic potential both in terms of ease of administration and targeting as well as increased bioavailability. Loop 6, as we have demonstrated in this study, is particularly amenable to production by synthetic means as a function of its amino acid composition and small size. Moreover, since these small peptides are derived from naturally occurring proteins, they may possess the feature of reduced toxicity or other side effects (Folkman et al., 2001).

There remain a number of critical yet unsolved questions with respect to the TIMPs and their important yet diverse biological functions (Brew et al., 2000; Baker et al., 2002). Among these questions, Nagase and coworkers have highlighted the critical need for a better understanding of the structural relationship(s) between MMP inhibition, cell growth-stimulating and growth-inhibiting activities, and the inhibition of angiogenesis (Brew et al., 2000). The current report addresses these questions and establishes the structural determinants responsible for capillary endothelial cell growth-inhibition and the inhibition of angiogenesis in vivo by uncoupling these activities from the inhibition of MMP activity. In doing so, we have discovered Loop 6, a novel, potent inhibitor of angiogenesis.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

The Following References are Incorporated Herein by Reference:

Abcallah et al. *Biol. Cell.*, 85:1-7 (1995).
Amour, A., et al. Lett 435:39-44, (1998).
Anand-Apte, B., et al. Invest Ophthalmol. Vis. Sci. 38:817-823 (1997).
Ashton, A. W., et al. J Biol Chem 274:20805-20811, (1999).
Ausprunk, D. H., et al. *Microvasc. Res.* 14:53-65 (1997).
Baffour, et al. *J. Vasc. Surg.,* 16:181-91 (1992).
Baker, A. H., et al. J Cell Sci 115:3719-3727 (2002).
Baker, A. H., et al. Br J Cancer 79:1347-1355 (1999).
Battegay, *J. Mol. Med.,* 73, 333-346 (1995).
Bergers, G., et al. Nat Cell Biol 2:737-744 (2000).
Birkedai-Hansen, H. *Current Opinions in Cell Biol.* 7:728-735 (1995)
Bodden, M. K., et al. J Biol Chem 269:18943-18952 (1994).
Bond, M., et al. J Biol Chem 275:41358-41363 (2000).
Brand, K., et al. Cancer Res 60:5723-5730 (2000).
Brew, K., et al. Biochim Biophys Acta 1477:267-283 (2000).
Burt, H. M., et al. Cancer Lett 88:73-79 (1995).
Butler, G. S., et al. J Biol Chem 274:20391-20396 (1999).
Carmichael, D. F., et al. *Proc. Natl. Acad. Sci.* USA 83:2407-2411 (1986).
Clare, J. J. et al. *Gene* 105:205-212 (1991).
Connolly, D. T., et al. Anal Biochem 152:136-140 (1986).
Coussens, L. M., et al. Science 295:2387-2392 (2002).
DeClerck, T. A., et al. *J. Biol. Chem.* 264:17445-17453 (1989).
Derossi et al. *Restor. Neurol. Neuros.,* 8:7-10 (1995),
Docherty, A. J. P., et al. *Nature* 318:66-69 (1985).
Fang, J., et al. Proc Natl Acad Sci USA 97:3884-3889 (2000).
Felgner et al. *J. Biol. Chem.,* 269: 2550-2561 (1994).
Fernandez-Catalan, C. et al. Embo J 17:5238-5248 (1998).
Flusberg, D. A., et al. Mol Biol Cell 12:3087-3094 (2001).
Folkman, J., et al. Thromb Haemost 86: 23-33 (2001).
Folkman, J. et al. *J. Biol. Chem.* 267(16):10931-10934 (1992).
Folkman, J. *N. Engl. J. Med.,* 285:1182-1186 (1971).
Folkman, J. *N. Engl. J. Med.,* 333:1757-1763 (1995).
Gasson, J. C., et al. Nature 315:768-771 (1985).
Giannelli, G., et al. Science 277:225-228 (1997).
Goldberg, G. I., et al. *J. Biol. Chem.* 267:4583-4591 (1992).
Gomis-Ruth, F. X., et al. Nature 389:77-81 (1997).
Goukassian, D., et al. Faseb J 15:1877-1885 (2001).
Guedez, L., et al. Blood 92:1342-1349 (1998a).
Guedez, L., et al. J Clin Invest 102:2002-2010 (1998b).
Hanahan et al., *Cell,* 86, 353-364.
Hayakawa, T., et al. J Cell Sci 107:2373-2379 (1994).
Hayakawa, T., et al. *FEBS Lett.* 298:29-32 (1992).
Herron, G. S., et al. *J. Biol. Chem.* 261:2814-2828 (1986).
Hoegy, S. E., et al. J Biol Chem 276:3203-3214 (2001).
Howard, E. W., et al. *J. Biol. Chem.* 266:13064-13069 (1991).
Huang, S., Chen, et al. Mol Biol Cell 9:3179-3193 (1998).
Ikegaya, K., et al. Anal Chem 69:1986-1991 (1997).
Jain et al. *Nature Medicine,* 3:1203-1208 (1997).
Johnson, M. D., et al. J Cell Physiol 160:194-202 (1994).
Kai, H. S., et al. J Biol Chem 8:8 (2002).
Kalebic, T., et al. *Science* 221:281-283 (1983).
Koolwijk, P., et al. Blood 97:3123-3131 (2001).
Lemelli. *Nature,* 227:680-685 (1970).
Li, G., et al. Cancer Res 59:6267-6275 (1999).
Lim, M. S., et al. Ann NY Acad Sci 878:522-523 (1999).
Liotta, L. A., et al. *Cell* 64:327-336 (1991).
Matrisian, L. *Trends Genet.* 6:121-125 (1990).
Mignatti, P., et al. *J. Cell. Bio.* 108:671-682 (1989).
Monsky, W. L., et al. Cancer Res 53:3159-3164 (1993).
Montesano, R., et al. *Cell* 62:435-445 (1990).
Montesano, R. et al. *Cell* 42:469-477 (1985).
Moses, M. A., et al. *J. Cell. Biochem.* 47:230-235 (1991).
Moses, M. A., et al. *J. Cell. Biochem.* 47:1-6 (1991).
Moses, M. A. Cells 15:180-189 (1997).
Moses, M. A., et al. Biotechnology (NY) 9:630-634 (1991).
Moses, M. A., et al. Science 248:1408-1410 (1990).
Moses, M. A., et al. J Cell Biol 119:475-482 (1992).
Moses, M. A., et al. Proc Natl Acad Sci USA 96:2645-2650 (1999).
Murphy, A. N., et al. J Cell Physiol 157:351-358 (1993).
Murphy, G., et al. Biochemistry 30:8097-8102 (1991).
Murphy, G. et al. *Biochem. Biophys. Acta* 839:214-218 (1985).
Murray, J. B., et al. *J. Biol. Chem.* 261:4154-4159 (1986).
Muskett, F. W., et al. J Biol Chem 273:21736-21743 (1998).
Nyguyen, Q., et al. *Biochemistry* 33:2089-2095 (1994).
O'Reilly, M. S., et al. Cell 79:315-328 (1994).
O'Shea, M., et al. Biochemistry 31:10146-10152 (1992).
Olson, M. W., et al. J Biol Chem 272:29975-29983 (1997).

Partridge, C. A., et al. Am J Physiol 272:L813-822 (1997).
Pavloff, N., et al. *J. Biol. Chem.* 267-17321-17326 (1992).
Polverini et al. *Methods Enzymol.,* 198:440-450 (1991).
Pu, et al. *J. Surg. Res,* 54:575-83 (1993).
Sanger et al. *Proc. Natl. Acad. Sci.* USA, 74:136-140 (1986).
Smith, M. R., et al. Cytokine 9:770-780 (1997).
Sreekrishna, K., et al. *Biotechnology* 28:4117-4125 (1989).
Stetler-Stevenson, W. G., et al. FEBS Lett 296:231-234 (1992).
Stetler-Stevenson, W. G., et al. Semin Cancer Biol 7:147-154 (1996).
Stetler-Stevenson, W. G., et al. *J. Biol. Chem.* 29:17374-17378 (1989).
Stetler-Stevenson, W. G. *J. Biol. Chem.* 265(23):13933-13936 (1990).
Stricklin, G. P. *Collagen Relat. Res.* 6:219-228 (1986).
Sun, J., et al. Biochem Biophys Res Commun 238:920-924 (1997).
Takeshita, et al. *Circulation,* 90:228-234 (1994).
Takeshita, et al. *J. Clin. Invest.,* 93:662-70 (1994).
Takigawa, M., et al. *Biochem. Biophys. Res. Commun.* 171:1264-1271 (1990).
Tolley, S., et al. J Mol Biol 229:1163-1164 (1993).
Tolley, S. P., et al. *Proteins: Struc., Fuct., Genet.* 17:435-437 (1993).
Tschopp, J. J. *Biotechnology* 5:1305-1306 (1987).
Vedvick, T., et al. *J. Indust. Microbiol.* 7:199-202 (1991).
Vu, T. H., et al. Cell 93:411-422 (1998).
Werb, Z. Cell 91:439-442 (1997).
White, C. E. et al. *Structure* 2:1003-1005 (1994).
Wilhelm, S. M., et al. *J. Biol. Chem.* 264:17213-17221 (1989).
Willenbrock, F., et al. *Biochemistry* 32:4330-4337 (1993).
Williamson, R. A., et al. *Biochemistry* 33:11745-11759 (1994).
Wingfield, P. T., et al. J Biol Chem 274:21362-21368 (1999).
Woessner, J. F. *Ann. N.Y. Acad. Sci.* 732:11-21 (1994).
Yan, L., et al. J Biol Chem 2:2 (2001).
Yanagisawa-Miwa, et al. *Science* 257:1401-1403 (1992).

What is claimed is:

1. A polypeptide consisting of the amino acid sequence set forth in SEQ ID NO: 1.

2. A pharmaceutical composition comprising the polypeptide of claim 1 in a therapeutically effective amount capable of inhibiting endothelial cell proliferation.

3. A method of inhibiting angiogenesis in a subject having an angiogenic disease or disorder, or at risk for developing an angiogenic disease or disorder, which comprises administering to the subject the pharmaceutical composition of claim 2, wherein angiogenesis is inhibited.

4. The method of claim 3, wherein the angiogenesis disease or disorder is restenosis.

5. The method of claim 3, wherein the angiogenesis disease or disorder is cancer.

6. The method of claim 5, wherein the cancer is a solid tumor.

7. The method of claim 5, wherein the cancer is medullary thyroid cancer.

8. The method of claim 5, wherein the tumor is a tumor of the central nervous system.

9. The method according to claim 3, wherein the angiogenesis disease or disorder is an ophthalmologic disease or disorder.

10. The method of claim 9, wherein the ophthalmologic disease or disorder is retinopathy, diabetic retinopathy or macular degeneration.

11. The method of 3, wherein said administering is conducted in conjunction with chemotherapy.

12. A method of treating a subject having a tissue remodeling-associated condition comprising administering to the subject the pharmaceutical composition of claim 2.

13. The method of claim 12, wherein the tissue remodeling-associated condition is arthritis or rheumatoid arthritis.

14. The method of claim 3, wherein said administering is conducted in conjunction with other known angiogenesis inhibitors.

15. The method of claim 3, wherein said administering comprises intravenous, transdermal, intrasynovial, intramuscular, or oral administration.

16. The method of claim 3, wherein said administering comprises therapeutic administration.

17. The method of claim 3, wherein said risk for developing an angiogenic disease or disorder is determined by measuring levels of cancer marker protein.

18. The method of claim 17, wherein the cancer marker protein is selected from the group consisting of calcitonin, PSA, thymosin β-15, thymosin β-16, or matrix metalloproteinase (MMP).

19. An article of manufacture comprising packaging material and a pharmaceutical composition contained within said packaging material, wherein said pharmaceutical composition is capable of inhibiting angiogenesis in a tissue associated with a disease condition, wherein said packaging material comprises a label which indicates that said pharmaceutical composition can be used for treating disease conditions by inhibiting angiogenesis, and wherein said pharmaceutical composition comprises a polypeptide consisting of the amino acid sequence set forth in SEQ ID NO: 1, in a therapeutically effective amount capable of inhibiting endothelial cell proliferation.

* * * * *

SEQUENCE LISTING

```
<160> NUMBER OF SEQ ID NOS: 8

<210> SEQ ID NO 1
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Glu Cys Leu Trp Met Asp Trp Val Thr Glu Lys Asn Ile Asn Gly His
  1               5                  10                  15

Gln Ala Lys Phe Phe Ala Cys Ile
            20

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Arg Cys Pro Met Ile Pro Cys Tyr Ile
  1               5                  10

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Trp Tyr Arg Gly Ala Ala Pro Pro Lys Gln Glu Phe Leu Asp Ile
  1               5                  10                  15

Glu Asp Pro

<210> SEQ ID NO 4
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Ile Arg Ala Lys
  1               5

<210> SEQ ID NO 5
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys Thr Val Phe Pro Cys Leu Ser Ile Pro Cys Lys Leu Gln Ser Gly
  1               5                  10                  15

Thr His Cys Leu Trp Thr Asp Gln Leu Leu Gln Gly Ser Glu Lys Gly
             20                  25                  30

Phe Gln Ser Arg His Leu Ala Cys Leu Pro Arg Glu Pro Gly Leu Cys
         35                  40                  45

Thr Trp Gln Ser Leu Arg Ser Gln Ile Ala
     50                  55

<210> SEQ ID NO 6
<211> LENGTH: 67
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Cys Lys Ile Thr Arg Cys Pro Met Ile Pro Cys Tyr Ile Ser Ser Pro
  1               5                  10                  15

Asp Glu Cys Leu Trp Met Asp Trp Val Thr Glu Lys Asn Ile Asn Gly
             20                  25                  30

His Gln Ala Lys Phe Phe Ala Cys Ile Lys Arg Ser Asp Gly Ser Cys
         35                  40                  45

Ala Trp Tyr Arg Gly Ala Ala Pro Pro Lys Gln Glu Phe Leu Asp Ile
     50                  55                  60

Glu Asp Pro
 65

<210> SEQ ID NO 7
<211> LENGTH: 67
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Lys Ile Lys Ser Cys Tyr Tyr Leu Pro Cys Phe Val Thr Ser Lys
  1               5                  10                  15

Asn Glu Cys Leu Trp Thr Asp Met Leu Ser Asn Phe Gly Tyr Pro Gly
             20                  25                  30

Tyr Gln Ser Lys His Tyr Ala Cys Ile Arg Gln Lys Gly Gly Tyr Cys
         35                  40                  45
```

-continued

```
Ser Trp Tyr Arg Gly Trp Ala Pro Pro Asp Lys Ser Ile Ser Asn Ala
    50                  55                  60

Thr Asp Pro
 65

<210> SEQ ID NO 8
<211> LENGTH: 67
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Cys Gln Ile Thr Thr Cys Tyr Thr Val Pro Cys Thr Ile Ser Ala Pro
 1               5                  10                  15

Asn Glu Cys Leu Trp Thr Asp Trp Leu Leu Glu Arg Lys Leu Tyr Gly
                20                  25                  30

Tyr Gln Ala Gln His Tyr Val Cys Met Lys His Val Asp Gly Thr Cys
            35                  40                  45

Ser Trp Tyr Arg Gly His Leu Pro Leu Arg Lys Glu Phe Val Asp Ile
    50                  55                  60

Val Gln Pro
 65
```